United States Patent
Wang et al.

(10) Patent No.: US 10,500,290 B2
(45) Date of Patent: Dec. 10, 2019

(54) PEPTIDE REAGENTS AND METHODS FOR DETECTION AND TARGETING OF DYSPLASIA, EARLY CANCER AND CANCER

(71) Applicant: THE REGENTS OF THE UNIVERSITY OF MICHIGAN, Ann Arbor, MI (US)

(72) Inventors: Thomas D. Wang, Ann Arbor, MI (US); Juan Zhou, Ann Arbor, MI (US); Bishnu P. Joshi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/505,846

(22) PCT Filed: Aug. 21, 2015

(86) PCT No.: PCT/US2015/046314
§ 371 (c)(1),
(2) Date: Feb. 22, 2017

(87) PCT Pub. No.: WO2016/029125
PCT Pub. Date: Feb. 25, 2016

(65) Prior Publication Data
US 2017/0246324 A1   Aug. 31, 2017

Related U.S. Application Data

(60) Provisional application No. 62/040,590, filed on Aug. 22, 2014.

(51) Int. Cl.
| A61K 49/00 | (2006.01) |
| C07K 7/06 | (2006.01) |
| C07K 7/08 | (2006.01) |
| G01N 33/574 | (2006.01) |
| A61K 45/06 | (2006.01) |

(52) U.S. Cl.
CPC .......... *A61K 49/0056* (2013.01); *A61K 45/06* (2013.01); *A61K 49/0032* (2013.01); *A61K 49/0043* (2013.01); *C07K 7/06* (2013.01); *C07K 7/08* (2013.01); *G01N 33/57419* (2013.01); *G01N 2800/52* (2013.01)

(58) Field of Classification Search
CPC .............................. A61K 49/0056; C07K 7/06
See application file for complete search history.

(56) References Cited

U.S. PATENT DOCUMENTS

| 6,472,504 | B1 * | 10/2002 | Prockop | C07K 14/001 530/300 |
|---|---|---|---|---|
| 6,559,126 | B2 * | 5/2003 | Tournaire | C07K 5/0815 435/4 |
| 7,018,803 | B2 * | 3/2006 | Prockop | C07K 14/001 435/7.1 |
| 7,138,238 | B2 * | 11/2006 | Vodyanoy | C12N 15/1037 435/7.1 |
| 7,807,624 | B2 * | 10/2010 | Kenan | A61L 27/34 424/423 |
| 8,268,962 | B2 * | 9/2012 | Heemskerk | A61K 49/0032 530/329 |
| 8,362,203 | B2 * | 1/2013 | Cunningham | C07K 7/06 530/329 |
| 8,519,097 | B2 * | 8/2013 | Heemskerk | A61K 47/48238 435/69.7 |
| 8,901,276 | B2 * | 12/2014 | Wang | A61K 38/08 424/9.1 |
| 2002/0068697 | A1 * | 6/2002 | Tournaire | C07K 5/0815 514/8.1 |
| 2003/0040466 | A1 * | 2/2003 | Vodyanoy | C12N 15/1037 435/7.1 |
| 2003/0087315 | A1 * | 5/2003 | Prockop | C07K 14/001 435/7.9 |
| 2003/0166004 | A1 * | 9/2003 | Gyuris | A61K 38/08 435/7.1 |
| 2003/0171289 | A1 * | 9/2003 | Tournaire | C07K 5/0815 514/8.1 |
| 2007/0060521 | A1 * | 3/2007 | Jove | A61K 31/00 514/7.5 |
| 2007/0160644 | A1 * | 7/2007 | Kenan | A61L 27/34 424/423 |
| 2007/0231833 | A1 | 10/2007 | Arcidiacono et al. | |
| 2010/0184948 | A1 * | 7/2010 | Heemskerk | A61K 47/48238 530/322 |
| 2010/0260673 | A1 | 10/2010 | Cao et al. | |
| 2010/0310459 | A1 * | 12/2010 | Wang | A61K 49/0043 424/9.1 |

(Continued)

FOREIGN PATENT DOCUMENTS

WO   WO-2009/143023 A2   11/2009
WO   WO 2012/123018   * 9/2012  .............. C07K 7/06

OTHER PUBLICATIONS

Ai et al., Biological evaluation of a novel doxorubicin-peptide conjugate for targeted delivery to EGF receptor—overexpressing tumor cells. *Mol. Pharmaceutics*, 8(2): 375-86 (2011).

(Continued)

*Primary Examiner* — Amber D Steele
(74) *Attorney, Agent, or Firm* — Marshall, Gerstein & Borun LLP

(57) ABSTRACT

The present invention is directed to EGFR-specific peptide reagents, methods for detecting pre-cancer, early cancer and/or cancer using the peptide reagents, and methods for targeting pre-cancer cells, early cancer cells and/or cancer cells using the peptide reagents. In one aspect, the disclosure provides reagents consisting essentially of a peptide QRH-KPRE (SEQ ID NO: 1), HAHRSWS (SEQ ID NO: 2), YLTMPTP (SEQ ID NO: 3), TYPISFM (SEQ ID NO: 4), KLPGWSG (SEQ ID NO: 5), IQSPHFF (SEQ ID NO: 6), YSIPKSS (SEQ ID NO: 7), SHRNRPRNTQPS (SEQ ID NO: 8), NRHKPREKTFTD (SEQ ID NO: 9).

22 Claims, 19 Drawing Sheets
Specification includes a Sequence Listing.

(56) References Cited

U.S. PATENT DOCUMENTS

| | | | | |
|---|---|---|---|---|
| 2011/0021748 | A1* | 1/2011 | Cunningham | C07K 7/06 530/329 |
| 2012/0219505 | A1* | 8/2012 | Wang | A61K 38/08 424/9.2 |
| 2012/0322724 | A1* | 12/2012 | Heemskerk | A61K 47/48238 514/4.8 |
| 2013/0045539 | A1* | 2/2013 | Delenda | C12N 9/22 435/462 |
| 2013/0096070 | A1* | 4/2013 | Staecker | C07K 7/06 514/20.9 |
| 2013/0115226 | A1 | 5/2013 | Van Slyke et al. | |
| 2013/0131314 | A1* | 5/2013 | Gergely | C07K 7/08 530/327 |
| 2014/0066387 | A1* | 3/2014 | Gelain | C07K 7/06 514/21.4 |

OTHER PUBLICATIONS

Alencar et al., Colonic adenocarcinomas: near-infrared microcatheter imaging of smart probes for early detection—study in mice. *Radiology*, 244: 232-8 (2007).

Bansal et al., Correlation of epidermal growth factor receptor with morphological features of colorectal advanced adenomas: a pilot correlative case series. *Am. J. Med. Sci.* 340: 296-300 (2010).

Bhargava et al., EGFR gene amplification in breast cancer: correlation with epidermal growth factor receptor mRNA and protein expression and HER-2 status and absence of EGFR-activating mutations. *Mod Pathol.* 18: 1027-33 (2005).

Bianco et al., Rational bases for the development of EGFR inhibitors for cancer treatment. *Int. J. Biochem. Cell. Biol.* 39: 1416-31 (2007).

Cwirla et al., Peptides on phage: A vast library of peptides for identifying ligands. *Proc. Natl. Acad. Sci. USA*, 87:6378-6382 (1990).

Essler et al., Molecular specialization of breast vasculature: a breast-homing phage-displayed peptide binds to aminopeptidase P in breast vasculature. *Proc. Natl. Acad. Sci. USA*, 99: 2252-7 (2002).

Fields et al., Solid phase peptide synthesis utilizing 9-fluorenylmethoxycarbonyl amino acids. *Int J. Pept Protein Res.* 35:161-214 (1990).

Flora et al., Epidermal growth factor receptor (EGFR) gene copy number in colorectal adenoma-carcinoma progression. *Cancer Genet.* 205: 630-5 (2012).

Goetz et al., In vivo molecular imaging of colorectal cancer with confocal endomicroscopy by targeting epidermal growth factor receptor. *Gastroenterology*, 138:435-46 (2010).

Hanawa et al., EGFR protein overexpression and gene amplification in squamous cell carcinomas of the esophagus. *Int. J. Cancer*, 118: 1173-80 (2006).

Hinoi et al., Mouse model of colonic adenoma-carcinoma progression based on somatic Apc inactivation. *Cancer Res.* 67(20): 9721-30 (2007).

Hirsch et al., Epidermal growth factor receptor in non-small-cell lung carcinomas: correlation between gene copy number and protein expression and impact on prognosis. *J. Clin. Oncol.* 21: 3798-807 (2003).

Hsiung et al., Detection of colonic dysplasia in vivo using a targeted heptapeptide and confocal microendoscopy. *Nat. Med.* 14: 454-8 (2008).

Hung et al., Development of a mouse model for sporadic and metastatic colon tumors and its use in assessing drug treatment. *Proc. Natl. Acad. Sci. USA*, 107: 1565-70 (2010).

Jimeno et al., Coordinated epidermal growth factor receptor pathway gene overexpression predicts epidermal growth factor receptor inhibitor sensitivity in pancreatic cancer. *Cancer Res.* 68: 2841-9 (2008).

Joyce et al., Stage-specific vascular markers revealed by phage display in a mouse model of pancreatic islet tumorigenesis. *Cancer Cell*, 4: 393-403 (2003).

Kelly et al., Detection of invasive colon cancer using a novel, targeted, library-derived fluorescent peptide. *Cancer Res.* 64: 6247-51 (2004).

Lee et al., Targeting bladder tumor cells in vivo and in the urine with a peptide identified by phage display. *Mol. Cancer Res.* 5(1): 11-9 (2007).

Li et al., Affinity peptide for targeted detection of dysplasia in Barrett's esophagus. *Gastroenterology*, 139: 1472-80 (2010).

Li et al., Identification and characterization of a novel peptide ligand of epidermal growth factor receptor for targeted delivery of therapeutics. *FASEB J*, 19:1978-85 (2005).

Liu et al., In vivo targeting of colonic dysplasia on fluorescence endoscopy with near-infrared octapeptide. *Gut*, 62: 395-403 (2003).

Ludtke et al., In vivo selection and validation of liver-specific ligands using a new T7 phage peptide display system. *Drug Deliv.* 14: 357-69 (2007).

Macindoe et al., HexServer: an FFT-based protein docking server powered by graphics processors. *Nucleic Acids Res.* 38(S2):W445-9 (2010).

Messersmith et al., Targeting EGFR in colorectal cancer. *N. Engl. J. Med.* 359: 1834-6 (2008).

Ogiso et al., Crystal structure of the complex of human epidermal growth factor and receptor extracellular domains. *Cell*, 110: 775-87 (2002).

Pasqualini et al., Organ targeting in vivo using phage display peptide libraries. *Nature*, 380: 364-6 (1996).

Petsalaki et al., Accurate prediction of peptide binding sites on protein surfaces. *PLoS Comput. Biol.* 5:e1000335 (2009).

Porebska et al., Expression of the tyrosine kinase activity growth factor receptors (EGFR, ERB B2, ERB B3) in colorectal adenocarcinomas and adenomas. *Tumour Biol.* 21: 105-15 (2000).

Rego et al., Prognostic effect of activated EGFR expression in human colon carcinomas: comparison with EGFR status. *Br. J. Cancer*, 102: 165-72 (2010).

Reuter et al., Targeting EGF-receptor-signalling in squamous cell carcinomas of the head and neck. *Br. J. Cancer*, 96: 408-16 (2007).

Rowan et al., APC mutations in sporadic colorectal tumors: A mutational "hotspot" and interdependence of the "two hits". *Proc. Natl. Acad. Sci. USA*, 97: 3352-7 (2007).

Scott et al., Searching for peptide ligands with an epitope library. *Science*, 249: 386-90 (1990).

Seymour et al., Panitumumab and irinotecan versus irinotecan alone for patients with KRAS wild-type, fluorouracil-resistant advanced colorectal cancer (PICCOLO): a prospectively stratified randomised trial. *Lancet Oncol.* 14(8): 749-59 (2013).

Song et al., Novel peptide ligand directs liposomes toward EGF-R high-expressing cancer cells in vitro and in vivo. *FASEB J*, 23: 1396-404 (2009).

Spano et al., Impact of EGFR expression on colorectal cancer patient prognosis and survival. *Ann. Oncol.* 16: 102-8 (2005).

Sturm et al., Targeted imaging of esophageal neoplasia with a fluorescently labeled peptide: first-in-human results. *Sci. Transl. Med.* 5: 184ra61 (2013).

Su et al., Multiple intestinal neoplasia caused by a mutation in the murine homolog of the APC gene. *Science*, 256(5057): 668-70 (1992).

Van Cutsem et al., Cetuximab and chemotherapy as initial treatment for metastatic colorectal cancer. *N. Engl. J. Med.* 360: 1408-17 (2009).

Vogelstein et al., Cancer genome landscapes. *Science*, 339: 1546-58 (2013).

Zhou et al., EGFR overexpressed in colonic neoplasia can be detected on wide-field endoscopic imaging. *Clin. Transl. Gastroenterol.* 16: 1-11 (2015).

\* cited by examiner

SEQUENCE LISTING

```
<160> NUMBER OF SEQ ID NOS: 25

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Gln Arg His Lys Pro Arg Glu
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

His Ala His Arg Ser Trp Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Tyr Leu Thr Met Pro Thr Pro
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Thr Tyr Pro Ile Ser Phe Met
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Lys Leu Pro Gly Trp Ser Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Ile Gln Ser Pro His Phe Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Tyr Ser Ile Pro Lys Ser Ser
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Ser His Arg Asn Arg Pro Arg Asn Thr Gln Pro Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Asn Arg His Lys Pro Arg Glu Lys Thr Phe Thr Asp
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Thr Ala Val Pro Leu Lys Arg Ser Ser Val Thr Ile
1               5                   10
```

```
<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Gly His Thr Ala Asn Arg Gln Pro Trp Pro Asn Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Leu Ser Leu Thr Arg Thr Arg His Arg Asn Thr Arg
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Arg His Arg Asp Thr Gln Asn His Arg Pro Thr Asn
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

Ala Arg His Arg Pro Lys Leu Pro Tyr Thr His Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide

<400> SEQUENCE: 15

Lys Arg Pro Arg Thr Arg Asn Lys Asp Glu Arg Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide

<400> SEQUENCE: 16

Ser Pro Met Pro Gln Leu Ser Thr Leu Leu Thr Arg
1               5                   10
```

```
<210> SEQ ID NO 17
<211> LENGTH: 12
<212> TYPE: PRT
<213> ORGANISM: Artificial Sequence
<220> FEATURE:
<223> OTHER INFORMATION: Synthetic peptide

<400> SEQUENCE: 17

Asn His Val His Arg Met His Ala Thr Pro Ala Tyr
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Linker

<400> SEQUENCE: 18

Gly Gly Gly Ser Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Pro Glu His Lys Arg Arg Gln
1               5

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ccctcatagt tagcgtaacg                                               20

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Ser His Arg Asn Arg Pro Arg Asn Thr Gln Pro Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide

<400> SEQUENCE: 22

Cys Met Tyr Ile Glu Ala Leu Asp Lys Tyr Ala Cys
1               5                   10
```

```
<210> SEQ ID NO 23
<211> LENGTH: 12
<212> TYPE: PRT
<213> ORGANISM: Artificial Sequence
<220> FEATURE:
<223> OTHER INFORMATION: Synthetic peptide

<400> SEQUENCE: 23

Tyr His Trp Tyr Gly Tyr Thr Pro Gln Asn Val Ile
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Leu Ala Arg Leu Leu Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Val Arg Pro Met Pro Leu Gln
1               5
```

PEPTIDE REAGENTS AND METHODS FOR DETECTION AND TARGETING OF DYSPLASIA, EARLY CANCER AND CANCER

STATEMENT OF GOVERNMENT INTEREST

This invention was made with government support under Grant Nos. CA163059, CA142750 and CA136429 awarded by the National Institute of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 5,150 byte ACII (Text) file named "48509_SeqListing.txt," created on Aug. 21, 2015.

FIELD OF THE INVENTION

The present invention is directed to EGFR-specific peptide reagents, methods for detecting pre-cancer, early cancer, and cancer using the peptide reagents, and methods for targeting pre-cancer cells, early cancer cells and cancer cells using the peptide reagents.

BACKGROUND

Colorectal cancer (CRC) is one of the most common causes of cancer-related deaths in the world. Approximately 1,360,000 new cases were diagnosed globally in 2012, resulting in ~693,000 annual deaths. These numbers are expected to nearly double over the next 20 years with a rapid rise in obesity and more developing countries adopting a Western diet. Greater focus on early detection of pre-malignant lesions (dysplasia) is needed [Vogelstein et al., Science, 339: 1546-1558 (2013)].

Endoscopy is a frequently performed imaging exam that is widely accepted by patients and referring physicians. However, a significant miss rate of >25% has been found on back-to-back exams for grossly visible adenomatous polyps. Moreover, flat lesions can give rise to carcinoma, and has been found to be as high as 36% of all adenomas. Flat lesions have been found to be more aggressive than polyps, and five times more likely to harbor either in situ or submucosal carcinoma in some patient populations. Studies of outcomes also show that colonoscopy results in a minimal reduction in mortality for cancers that arise in the proximal colon (right side). Furthermore, cancer diagnosed after a "negative" colonoscopy occurs more frequently in the proximal colon. These findings have been attributed to greater genetic instability and a flat morphology. Thus, imaging methods that are sensitive to flat lesions may improve detection and prevention of CRC. Although colonoscopy is widely performed for screening, there is minimal reduction in mortality for carcinomas that arise in the proximal colon. Furthermore, cancer diagnosed after a "negative" colonoscopy occurs more frequently in the proximal colon. These findings have been attributed to greater microsatellite instability and a flat morphology.

Pre-clinical mouse models of disease provide an important tool for studying mechanisms of disease development. It has been established that mutations in the adenomatous polyposis coli (APC) gene are likely to be critical events in the initiation of the majority of adenomas and CRC. Previously-reported genetically engineered mouse models that mimic human APC gene mutations mainly develop adenomas in the small intestine [e.g., $APC^{Min}$ model, Su et al., Science 256(5057):668-670 (1992)], not the distal colon, making it difficult to image the polyps and their progression in vivo using currently available small animal endoscopy tools. Hinoi et al., Cancer Res., 67(20): 9721-9730 (2007) describes genetically engineered mice (termed CPC:Apc mice) in which a somatic mutation in an Apc allele leads to a truncated Apc protein and causes the development of adenomas in the distal colon as early as 10 weeks. Others have developed mouse models that grow tumors in the distal colon using implantation of cancerous cells [Alencar et al., Radiology, 244: 232-238 (2007)] or adenovirus activated mutations [Hung et al., Proc. Natl. Acad. Sci. USA, 107: 1565-1570 (2010)] and report binding of cathepsin B smart probes, but surgical intervention was needed to generate polyps and the ensuing response to injury may have resulted in target alteration.

Endoscopic imaging with use of exogenous fluorescent-labeled probes, is a promising method for achieving greater specificity in the detection of neoplastic lesions by identifying the expression of unique molecular targets. Imaging provides precise localization, and fluorescence provides improved contrast. Previously, several diagnostic molecules have been used as targeted agents, including antibodies and antibody fragments, for the detection of pre-malignant and malignant lesions in various types of cancer. However, the use of antibodies and antibody fragments is limited by immunogenicity, cost of production and long plasma half-life. Small molecules, RNA aptamers, and activatable probes have also been used. Peptides represent a new class of imaging agent that is compatible with clinical use in the digestive tract, in particular with topical administration.

Phage display is a powerful combinatorial technique for peptide discovery that uses methods of recombinant DNA technology to generate a complex library of peptides, often expressing up to 107-109 unique sequences, that can bind to cell surface antigens. The DNA of candidate phages can be recovered and sequenced, elucidating positive binding peptides that can then be synthetically fabricated. Phage display identified peptide binders to high grade dysplasia in Barrett's esophagus [Li et al., Gastroenterology, 139:1472-80 (2010)] and human colonic dysplasia [Hsiung et al., Nat. Med., 14: 454-458 (2008)] using the commercially available NEB M13 phage system. The T7 system has proven effective in in vivo panning experiments identifying peptides specific to pancreatic islet vasculature [Joyce et al., Cancer Cell, 4: 393-403 (2003)], breast vasculature [Essler and Ruoslahti, Proc. Natl. Acad. Sci. USA, 99: 2252-2257 (2002)], bladder tumor cells [Lee et al., Mol. Cancer Res., 5(1): 11-19 (2007)], and liver tissue [Ludtke et al., Drug Deliv., 14: 357-369 (2007)]. Panning with intact tissue presents additional relevant cell targets while accounting for subtle features in the tissue microenvironment that may affect binding.

Epidermal growth factor receptor (EGFR) is a transmembrane tyrosine kinase that stimulates normal epithelial cell growth and differentiation. Ligand binding to the EGFR extracellular domains 1 and 3 results in receptor dimerization and autophosphorylation. Overexpression of EGFR has been reported in a number of cancers, including brain, breast, lung, colon, esophagus, stomach, liver, ovary, biliary duct, and pancreas. Amplifications of EGFR or family members are found in about 30% of all epithelial cancers. This cell surface receptor plays an important role in the development of a number of epithelial-derived cancers [Bianco et al., *Int. J. Biochem. Cell. Biol.*, 39: 1416-1431 (2007)], and is an important target for CRC therapy. [Van Cutsem et al., *N. Engl. J. Med.*, 360: 1408-1417 (2009); Seymour et al., *Lancet Oncol.*, PMID 32725851 (2013) In azoxymethane induced animal models of CRC, EGFR signaling was required to form adenomas in mice, and was shown to promote flat lesions in aberrant crypt foci in the colon of rats. In humans, overexpression of EGFR has been reported in as high as 97% of colonic adenocarcinomas [Spano et al., *Ann. Oncol.*, 16: 102-108 (2005); Porebska et al., *Tumour Biol.*, 21: 105-115 (2000)]. Adenomas with high-grade dysplasia and villous features on histology have been shown to exhibit increased expression of EGFR on immunohistochemistry [Bansal et al., *Am. J. Med. Sci.*, 340: 296-300 (2010)]. Furthermore, EGFR gene copy number has been found to increase with histological progression of disease [Flora et al., *Cancer Genet.*, 205: 630-635 (2012); Rego et al., *Br. J. Cancer*, 102: 165-172 (2010)]. Targeted therapies for EGFR include monoclonal antibodies (cetuximab, panitumumab) and small molecule inhibitors (gefitinib, erlotinib). Currently, patient eligibility criteria for EGFR therapy are based on qualitative evaluation of EGFR expression levels on immunohistochemistry.

New products and methods for early detection of pre-cancer (dysplasia), early cancer and cancer are needed in the art. New products and methods for early detection would have important clinical applications for increasing the survival rate for CRC and other epithelial cell-derived cancers, and reducing the healthcare costs.

SUMMARY

In one aspect, the disclosure provides reagents consisting essentially of a peptide QRHKPRE (SEQ ID NO: 1), HAHRSWS (SEQ ID NO: 2), YLTMPTP (SEQ ID NO: 3), TYPISFM (SEQ ID NO: 4), KLPGWSG (SEQ ID NO: 5), IQSPHFF (SEQ ID NO: 6), YSIPKSS (SEQ ID NO: 7), SHRNRPRNTQPS (SEQ ID NO: 8), NRHKPREKTFTD (SEQ ID NO: 9), TAVPLKRSSVTI (SEQ ID NO: 10), GHTANRQPWPND (SEQ ID NO: 11), LSLTRTRHRNTR (SEQ ID NO: 12), RHRDTQNHRPTN (SEQ ID NO: 13), ARHRPKLPYTHT (SEQ ID NO: 14), KRPRTRNKDERR (SEQ ID NO: 15), SPMPQLSTLLTR (SEQ ID NO: 16) or NHVHRMHATPAY (SEQ ID NO: 17), or a multimer form of the peptides, wherein the reagents specifically bind to EGFR. In some embodiments, the multimer form is a dimer.

In some embodiments, the reagent comprises a detectable label attached to the peptide. In some embodiments, the detectable label is detectable by microscopy, photoacoustic, ultrasound or magnetic resonance imaging. In some embodiments, the label detectable by microscopy is fluorescein isothiocyanate (FITC), Cy5, Cy5.5 or IRdye800. In some embodiments, the detectable label is attached to the peptide by a peptide linker. In some embodiments, the terminal amino acid of the linker is lysine. In some embodiments, the linker comprises the sequence GGGSK set out in SEQ ID NO: 18.

In some embodiments, the reagent comprises a therapeutic moiety attached to the peptide. In some embodiments, the therapeutic moiety is chemotherapeutic agent.

In another aspect, the disclosure provides a composition comprising a reagent of the invention and a pharmaceutically acceptable excipient.

In yet another aspect, the disclosure provides methods for detecting colon dysplasia, early cancer or cancer in a patient comprising the steps of administering a reagent of the invention to the colon of the patient and detecting binding of the reagent to dysplastic cells.

In still another aspect, the disclosure provides a method for detecting dysplasia, early cancer or cancer in a patient comprising the steps of administering a reagent of the invention to the patient and detecting binding of the reagent. In another aspect, the disclosure provides a method of determining the effectiveness of a treatment for cancer and/or cancer metastasis, or recurrence of cancer in a patient comprising the step of administering a reagent of the invention to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, the methods further comprise obtaining a biopsy of the cells labeled by the reagent.

In yet another aspect, the disclosure provides a method for delivering a therapeutic moiety to dysplastic cells of a patient comprising the step of administering a reagent of the invention to the patient.

In still another aspect, the disclosure provides a method for delivering a therapeutic moiety to early cancer cells or cancer cells of a patient comprising the step of administering a reagent of the invention to the patient.

In the methods of each aspect described herein, dysplasia, early cancer or cancer arising from epithelial cells in, for example, colon, brain, breast, prostate, liver, lung, esophagus, stomach, bladder, bile duct and skin is specifically contemplated.

In a further aspect, the disclosure provides a kit for administering a composition of the invention to a patient in need thereof, comprising the composition, instructions for use of the composition and a device for administering the composition to the patient.

In another aspect, the disclosure provides a peptide consisting of the amino acid sequence QRHKPRE (SEQ ID NO: 1), HAHRSWS (SEQ ID NO: 2), TYPISFM (SEQ ID NO: 4), SHRNRPRNTQPS (SEQ ID NO: 8), NRHKPREKTFTD (SEQ ID NO: 9), TAVPLKRSSVTI (SEQ ID NO: 10), GHTANRQPWPND (SEQ ID NO: 11), LSLTRTRHRNTR (SEQ ID NO: 12), RHRDTQNHRPTN (SEQ ID NO: 13), ARHRPKLPYTHT (SEQ ID NO: 14) or KRPRTRNKDERR (SEQ ID NO: 15).

DESCRIPTION

Figure 1:
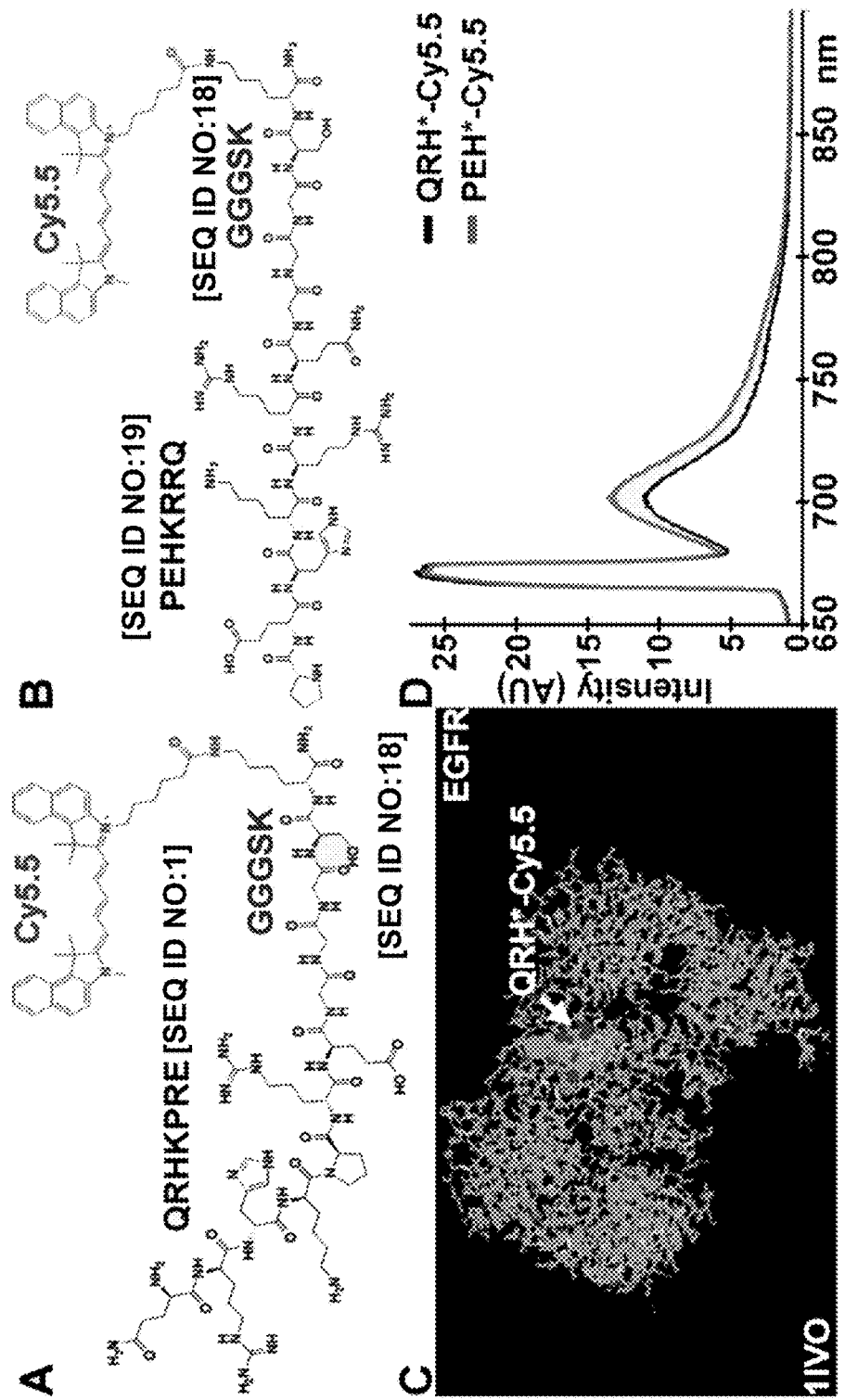
FIG. 1 shows a peptide specific for EGFR. A) Chemical structure of QRHKPRE peptide (black) (SEQ ID NO: 1) with GGGSK linker (blue) (SEQ ID NO: 18) and Cy5.5 fluorophore (red). B) Scrambled peptide PEHKRRQ (control) (SEQ ID NO: 19). C) QRH*-Cy5.5 was found to bind domain 2 of EGFR (1IVO) on structural model. D) Fluorescence spectra with $\lambda_{ex}$=671 nm shows peak emission near 710 nm.

Transformed cells and tissues express molecular changes well in advance of gross morphological changes, thus providing a unique opportunity for the early detection of cancer. Peptides that bind to pre-cancerous lesions have the potential to guide tissue biopsy for lesions that are endoscopically "invisible." Peptides have in vivo advantages because they can be delivered topically to identify early molecular changes on the surface of epithelial cells where cancer originates. In addition, they can exhibit rapid binding kinetics and also diffuse into diseased tissue.

In one aspect, the invention provides peptides that bind to EGFR expressed on dysplastic cells and/or cancerous cells. The peptides include, but are not limited to, the peptides QRHKPRE (SEQ ID NO: 1), HAHRSWS (SEQ ID NO: 2), YLTMPTP (SEQ ID NO: 3), TYPISFM (SEQ ID NO: 4), KLPGWSG (SEQ ID NO: 5), IQSPHFF (SEQ ID NO: 6), YSIPKSS (SEQ ID NO: 7), SHRNRPRNTQPS (SEQ ID NO: 8), NRHKPREKTFTD (SEQ ID NO: 9), TAVPLKRSSVTI (SEQ ID NO: 10), GHTANRQPWPND (SEQ ID NO: 11), LSLTRTRHRNTR (SEQ ID NO: 12), RHRDTQNHRPTN (SEQ ID NO: 13), ARHRPKLPYTHT (SEQ ID NO: 14), KRPRTRNKDERR (SEQ ID NO: 15), SPMPQLSTLLTR (SEQ ID NO: 16) and NHVHRMHATPAY (SEQ ID NO: 17).

In a further aspect, the invention provides reagents comprising a peptide of the invention. A "reagent" of the invention comprises at least two components, a peptide of the invention and another moiety attached to the peptide. The only component of the reagent that contributes to binding of EGFR is the peptide of the invention. In other words, the reagent "consists essentially of" a peptide of the invention. In some embodiments, the other moiety comprises amino acids but the peptide of the invention is not linked to those amino acids in nature and the other amino acids do not affect binding of the peptide to EGFR. Moreover, the other moiety in a reagent contemplated herein is not a phage in a phage display library or a component of any other type of peptide display library.

In some embodiments, the reagents comprise a detectable label as a moiety attached to a peptide of the invention. The detectable label may be detectable, for example, by microscopy, photoacoustic, ultrasound, PET, SPECT, or magnetic resonance imaging. In some embodiments the label detectable by microscopy is fluorescein isothiocyanate (FITC), Cy5, Cy5.5 and IRdye800.

In some embodiments, the detectable label is attached to a peptide of the invention by a peptide linker. The terminal amino acid of the linker by be a lysine such as in the exemplary linker GGGSK (SEQ ID NO: 18).

In some embodiments, the reagents comprise a therapeutic moiety attached to a peptide of the invention. The therapeutic moiety may be a chemopreventative or chemotherapeutic agent. In certain embodiments, the therapeutic moiety is celecoxib, 5-fluorouracil, and/or chlorambucil.

In yet a further aspect, the invention provides a composition comprising a reagent of the invention and a pharmaceutically acceptable excipient.

In still a further aspect, the invention provides a method for specifically detecting pre-cancer, early cancer and/or cancer in a patient comprising the steps of administering a reagent comprising a peptide of the invention attached to a detectable label to the patient and detecting binding of the reagent to dysplastic cells or early cancer cells. In some embodiments, the detectable binding takes place in vivo. In others, the detectable binding takes places in vitro. In still others, the detectable binding takes place in situ. Detection of pre-cancer (dysplasia), early cancer and/or cancer arising from epithelial cells is specifically contemplated.

"Pre-cancer" (or "pre-cancerous cells") and "dysplasia" (or "dysplastic cells") are used interchangeably herein. "Cancer" is used herein to refer to metastatic/invasive cancer, distinguishing "cancer" from "early cancer" as used herein, The phrase "specifically detects" means that the reagent binds to and is detected in association with a type of cell, and the reagent does not bind to and is not detected in association with another type of cell at the level of sensitivity at which the method is carried out.

In the colon, the transformation from pre-malignant mucosa to carcinoma involves the development of flat and depressed (non-polypoid) lesions, adenomatous polyps (polypoid lesions) and then frank carcinoma (colon cancer cells). Detecting colon dysplasia (i.e., dysplastic cells), pre-cancerous cells and/or cancerous cells according to the invention includes detecting binding to flat and depressed lesions, adenomatous polyps and/or cancer cells. In some embodiments, a reagent of the invention specifically detects cells of flat and depressed lesions. In some embodiments, a reagent of the invention specifically detects cells of adenomatous polyps. In some embodiments, a reagent of the invention specifically detects colon cancer cells. In some embodiments, a reagent of the invention may specifically detect two or more of cells of flat and depressed lesions, cells of adenomatous polyps and colon cancer cells.

Flat dysplastic lesions are also observed in the setting of chronic ulcerative colitis and are also contemplated to be detectable by methods of the invention.

In an additional aspect, the invention provides a method of determining the effectiveness of a treatment for cancer and/or cancer metastasis, or recurrence of cancer in a patient comprising the step of administering a reagent comprising a peptide of the invention attached to a detectable label to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment. In some embodiments, the method further comprises obtaining a biopsy of the cells labeled by the reagent.

In another aspect, the invention provides a method for delivering a therapeutic moiety to a patient comprising the step of administering a reagent comprising a peptide of the invention attached to a therapeutic moiety to the patient.

In yet another aspect, the invention provides a method for delivering a therapeutic moiety to colon early cancer cells or cancer cells of a patient comprising the step of administering a reagent comprising a peptide of the invention attached to a therapeutic moiety to the colon of the patient.

In still another aspect, the invention provides a kit for administering a composition of the invention to a patient in need thereof, where the kit comprises a composition of invention, instructions for use of the composition and a device for administering the composition to the patient.

Linkers, Peptides and Peptide Analogs

As used herein, a "linker" is a sequence of amino acids located at the C-terminus of a peptide of the disclosure. In some embodiments, the linker sequence terminates with a lysine residue.

In some embodiments, the presence of a linker results in at least a 1% increase in detectable binding of a reagent of the invention to dysplastic colon cells or cancerous colon cells compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the invention may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure have been developed using techniques of phage display, a powerful combinatorial method that uses recombinant DNA technology to generate a complex library of polypeptides for selection by preferential binding to cell surface targets [Scott et al., *Science,* 249:386-390 (1990)]. The protein coat of bacteriophage, such as the filamentous M13 or icosahedral T7, is genetically engineered to express a very large number ($>10^9$) of different polypeptides with unique sequences to achieve affinity binding [Cwirla et al., *Proc. Natl. Acad. Sci. USA,* 87:6378-6382 (1990)]. Selection is then performed by biopanning the phage library against cultured cells and tissues that over express the target. The DNA sequences of these candidate phage are then recovered and used to synthesize the polypeptide [Pasqualini et al., *Nature,* 380:364-366 (1996)]. The polypeptides that preferentially bind to dysplastic mucosa are optionally labeled with fluorescence dyes, including but not limited to, FITC, Cy 5.5, Cy 7, and Li-Cor. These polypeptide-dye reagents have been developed and have demonstrated preferential binding to colon cancer (HT29) cells in culture and to pre-clinical xenograft models [Kelly et al., *Cancer Res.,* 64:6247-51 (2004)].

Peptides include D and L forms, either purified or in a mixture of the two forms. Also contemplated by the present disclosure are peptides that compete with peptides of the invention for binding to colon cells.

In some embodiments, a peptide of a reagent of the invention is presented in multimer form (e.g., as a dimer, trimer, etc.). Various scaffolds are known in the art upon which multiple peptides can be presented. In some embodiments, a peptide is presented in multimer form on a trilysine dendritic wedge. In an exemplary embodiment herein, peptide QRHKPRE (SEQ ID NO: 1) is presented in dimer form on lysine. Other scaffolds known in the art include, but are not limited to, other dendrimers and polymeric (e.g., PEG) scaffolds.

It will be understood that peptides and linkers of the invention optionally incorporate modifications known in the art and that the location and number of such modifications are varied to achieve an optimal effect.

In some embodiments, the compound is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-$NO_2$)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to dysplastic cells or early cancer cells in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to dysplastic cells or early cancer cells in comparison to the parent peptide.

Detectable Markers

As used herein, a "detectable marker" is any label that can be used to identify the binding of a composition of the disclosure to dysplastic cells or early cancer cells. Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source.

Fluorophores, chemical and protein tags that are contemplated for use in the invention include, but are not limited to, FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 $Ca^{2+}$, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red $Ca^{2+}$, Fura Red, high Ca, Fura Red, low Ca, Fura-2 Ca2+, Fura-2, Fura-2, GFP (S65T), HcRed, Indo-1 $Ca^{2+}$, Indo-1, Ca free, Indo-1, Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Niss1 stain-RNA, Nile Blue, Nile Red, Nile Red-lipid, Niss1, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca$^+$, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na$^+$, Sodium Green Na$^+$, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the invention include radiolabels. For example and without limitation, radiolabels that contemplated in the compositions and methods of the present disclosure include $^{11}$C, $^{13}$N, $^{15}$O, $^{18}$F, $^{32}$P, $^{52}$Fe, $^{62}$Cu, $^{64}$Cu, $^{67}$Cu, $^{67}$Ga, $^{68}$Ga, $^{86}$Y, $^{89}$Zr, $^{90}$Y, $^{94}$mTc, $^{94}$Tc, $^{95}$Tc, $^{99}$mTc, $^{103}$Pd, $^{105}$Rh, $^{109}$Pd, $^{111}$Ag, $^{111}$In, $^{123}$I, $^{124}$I, $^{125}$I, $^{131}$I, $^{140}$La, $^{149}$Pm, $^{153}$Sm, $^{154-159}$Gd, $^{165}$Dy, $^{166}$Dy, $^{166}$Ho, $^{169}$Yb, $^{175}$Yb, $^{175}$Lu, $^{177}$Lu, $^{186}$Re, $^{188}$Re, $^{192}$Ir, $^{198}$Au, $^{199}$Au, and $^{212}$Bi.

A worker of ordinary skill in the art will appreciate that there are many such detectable markers that can be used to visualize a composition of the disclosure, in vitro, in vivo or ex vivo.

Therapeutic Moieties

Therapeutic moieties contemplated by the invention include, but are not limited to polypeptides (including protein therapeutics) or peptides, small molecules, therapeutic agents, chemotherapeutic agents, or combinations thereof.

The term "small molecule", as used herein, refers to a chemical compound, for instance a peptidometic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some embodiments, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In some embodiments, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, in some embodiments, chemotherapeutic agents. A chemotherapeutic agent contemplated for use in a reagent of the invention includes, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, *vinca* alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Gefitinib and erlotinib are also specifically contemplated.

Dosages of the therapeutic moiety provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the invention sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to dysplastic cells, early cancer cells or cancer cells is by any means known to those of ordinary skill in the art. As discussed herein, visualization is, for example and without limitation, in vivo, in vitro, or in situ visualization.

In some embodiments where the detectable label is a radiolabel, the radiolabel is detected by nuclear imaging. Nuclear imaging is understood in the art to be a method of producing images by detecting radiation from different parts of the body after a radioactive tracer material is administered. The images are recorded on computer and on film.

Some embodiments of methods of the invention involve the acquisition of a tissue sample from a patient. The tissue sample is selected from the group consisting of a tissue or organ of said patient.

Formulations

Compositions of the invention are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one compound as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

EXAMPLES

The invention will be more fully understood by reference to the following examples which detail exemplary embodiments of the invention.

Materials and Methods Used in the Examples

Cells, Chemicals and Materials

Human colorectal adenocarcinoma (HT29, SW480, and SW620) cells were obtained from the American Type Culture Collection (ATCC, Manassas, Va.). We used McCoy's Medium for HT29 cells and Dulbecco's Modified Eagle Medium (DMEM) for SW480 and SW620 cells. All cells were cultured at 37° C. in 5% $CO_2$, and supplemented with 10% fetal bovine serum (FBS) and 1% penicillin/streptomycin. Penicillin/streptomycin was omitted for the siRNA knockdown studies. The cells were passaged using 0.25% EDTA containing trypsin (Mediatech Inc, Manassas, Va.). The number of cells were determined on a hemocytometer. For Chinese Hamster Ovary (CHO) cells, we used MEMα (□□Life Technologies, #12561) with 10 μg/mL glycine, 2 Mm/L glutamine, 15 μg/mL hypoxanthine and 5 μg/mL thymidine for culture and serum-free cell culture media (Thermo Scientific, HyClone™ SFM4CHO™) for producing the EGFR-ECD protein. Peptide synthesis reagents were obtained from Anaspec (Anaspec, Fremont, Calif.) or AAPPTEC (AAPPTEC, Louisville, Ky.) and were of the highest grade available (>99% purity) and used without further purification. Solvents and other chemical reagents were purchased from Sigma-Aldrich unless otherwise mentioned.

Confocal Fluorescence Microscopy

HT29, SW480, and SW620 cells (~$10^3$) were grown on cover slips to ~80% confluence. The cells were washed 1× with PBS and incubated with 5 µM of QRH*-Cy5.5 and PEH*-Cy5.5 for 3 min at RT. The cells were then washed 3× in PBS, fixed with 4% paraformaldehyde (PFA) for 5 min, washed 1× with PBS, and then mounted on glass slides with ProLong Gold reagent containing DAPI (Invitrogen). Confocal fluorescence images were collected with FITC, Cy5.5, and DAPI filters (Leica Inverted SP5X Confocal Microscope System) using a 63× oil-immersion objective. Fluorescence intensities from 5 cells in 2 independent images were quantified using custom Matlab (Mathworks) software.

Statistical Analysis

For the in vivo fluorescence images of mouse colon, the T/B ratios for flat dysplasia and polyps were log-transformed to improve normality. The fold-change between classification pairs was estimated using the anti-log of the difference in the log-transformed data. Differences in results between the experimental and control peptides were evaluated on t-test. *P≤0.05 was considered significant. Similar methods were used to evaluate the ex vivo fluorescence images of human colonic specimens. The results were plotted on a receiver-operator characteristic (ROC) curve. Co-localization of peptide and antibody binding was evaluated on Pearson's correlation coefficient. All analyses were performed using custom Matlab software (MathWorks Inc).

Example 1

Expression of EGFR Extracellular Domain (ECD)

The extracellular domain (ECD) of EGFR (amino acids 1-645 in domains 1-4) was cloned into the pDual GC mammalian expression vector (Stratagene, #214503). The gene was inserted between two Eam1104 I restriction sites, resulting in one directional ligation. A CMV promoter drives protein expression in mammalian cells. Myc and His tags were expressed in-frame on the C-terminus of the recombinant EGFR-ECD for use in protein characterization and purification, respectively. A thrombin recognition site between EGFR-ECD and myc-His allows for the tags to be cleaved after use. Correct construction was verified by DNA sequencing. The construct was first transiently transfected into HEK-293T cells and verified on Western blot. The construct was then introduced into Chinese Hamster Ovary (CHO) cells grown in MEMα. Stable clones were established by Geneticin selection, and those with the highest expression levels were expanded and cultured in serum-free cell media to produce EGFR-ECD in microgram quantities for biopanning.

The recombinant proteins were purified with cobalt affinity chromatography using a TALON metal affinity resin (Clontech, #635503). The elution was concentrated with an Amicon Ultra-15 centrifugal filter unit with Ultracel-30 membrane (Millipore, #UFC03024) and dialyzed in thrombin cleavage buffer (Sigma-Aldrich, T9685). The myc and His tags were removed using a thrombin CleanCleave kit (Sigma-Aldrich, #RECOMT). ECD-EGFR was further purified with a gel filtration column (GE Healthcare, HiLoad 16/600 Superdex 200 pg). The final protein was concentrated, dialyzed in 0.1 M $NaHCO_3$ buffer, and quantified by SDS-PAGE using BSA as a control.

Figure 11:
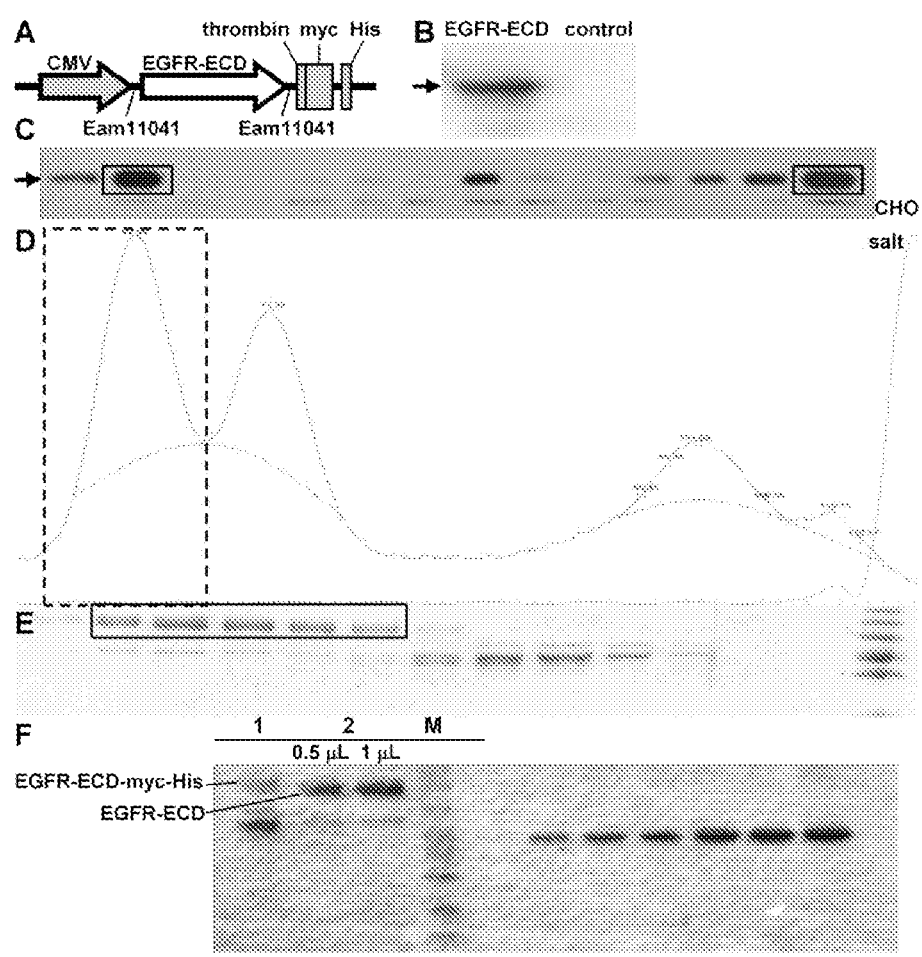
FIG. 11 relates to the expression of EGFR extracellular domain (ECD). A) Construct consisting of EGFR extracellular domain (ECD) linked via a thrombin recognition site to myc and His tag was cloned into pDual GC expression vector. Expression of EGFR-ECD (arrows) shown on Western using myc tag from B) transient transfection in HEK293T and C) stable transfection in CHO cells. Clones with highest levels of expression (boxes) were expanded. D) Affinity purification was performed using His-tag based cobalt chromatography, and peak for EGFR-ECD (dashed box) was further purified. E) Bands for EGFR-ECD (box) were identified on SDS-PAGE. F) Coomassie blue stain shows bands 1) before and 2) after purification with tag cleavage (0.5 and 1 µL). Protein marker (M).

Thus, we used the pDual GC mammalian system to express the extracellular domain (ECD) of EGFR, FIG. 11A. EGFR-ECD represents the exposed region of the target that can be accessed on imaging, and was linked in frame via a thrombin cleavage site to a myc-His tag. We used myc to confirm (transient) expression of the recombinant protein in HEK293T cells on Western, FIG. 11B, before a stable transfection was performed in CHO cells. Clones with the highest levels of protein expression (solid boxes) on Western were expanded, FIG. 11C. Affinity purification was performed using His-tag based cobalt chromatography. The elution was first verified on SDS-PAGE and then cleaved with thrombin to remove the myc-His tag. Further purification was performed on gel filtration, and the EGFR-ECD peak (dashed box) was identified, FIG. 11D. The corresponding bands (solid box) on SDS-PAGE were selected and concentrated. We produced 600 µg of EGFR-ECD with >90% purity, FIG. 11F.

Example 2

Peptides Specific for EGFR

Peptide selection was performed per manufacturer instructions using a phage display library (New England Biolabs, Ph.D.-12) that consists of M13 bacteriophage that expresses about $10^9$ unique 12-amino acid sequences. The phage library ($2 \times 10^{11}$ pfu consisting of $2 \times 10^9$ unique clones with about [H]1 00 copies each) was biopanned against the purified recombinant EGFR-ECD proteins immobilized in a 6-well plate at 4° C. The biopanning was performed with the known protein target (EGFR-ECD) as opposed to the unbiased approach performed in Li et al., Gastroenterology, 139:1472-80 (2010). Four rounds of biopanning were performed using a decreasing quantity (100, 80, 60, and 40 µg) of EGFR-ECD in successive rounds to increase binding specificity. After four rounds of biopanning, fifty phage colonies were randomly selected for DNA preparation and sequencing analysis. These sequences were analyzed with an ABI Automatic DNA Analyzer (Applied Biosystems) using the primer 5'-CCCTCATAG TTA GCG TAA CG-3' (SEQ ID NO:20); –96 glll sequencing primer, New England Biolabs) that corresponds to the plll gene sequence of the M13 phage.

We used PepSite software [Petsalaki et al., *PLoS Comput Biol*, 5:e1000335 (2009)] to evaluate binding of the candidate sequences to the crystal structure of the extracellular domain of inactive, monomeric EGFR (code: 1IVO) obtained from the RCSB Protein Data Bank. 3D biochemical structures of the peptides were created using Chembiodraw software (Perkin Elmer). To achieve the highest specificity, we mutated the peptide sequences obtained from biopanning to align with the pdb structure of EGFR extracellular domain. For example, we chose the first seven amino acids of the candidate sequence NRHKPREKTFTD (SEQ ID NO: 9), and mutated first N to Q to generate the peptide sequence QRHKPRE (SEQ ID NO: 1). We then validated alignment of Cy5.5-labeled peptides on a structural model (Hex 6.3, Inria) [Macindoe et al., *Nucleic Acids Research*, 38(S2):W445-W449 (2010)] by rotating the receptor and ligand about their centers of mass over a full range of intermolecular distances and rotational angles.

Figure 12:
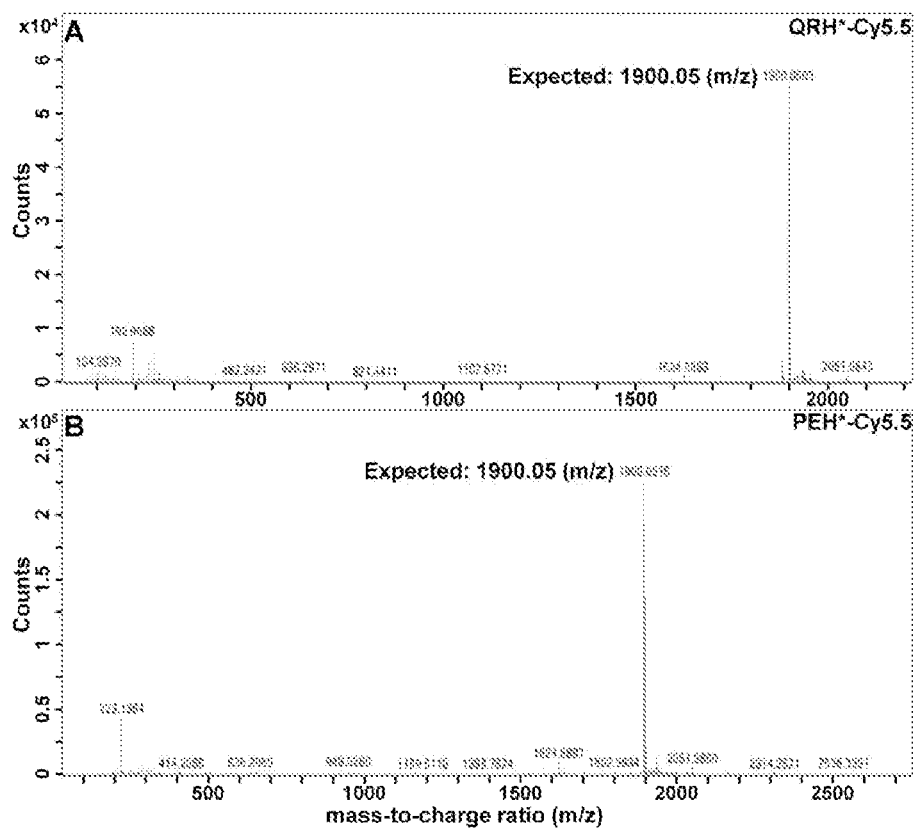
FIG. 12 shows mass spectrometry of Cy5.5-labeled peptides. On mass spectrometry, the experimental mass-to-charge (m/z) ratios for A) QRH*-Cy5.5 and B) PEH*-Cy5.5 were found to be 1900.05, and agreed with the expected values.

Using the structural model described in Petsalaki et al., supra, we found a minimum docking energy of $E_t$=–504.1 for QRHKPRE (SEQ ID NO: 1) labeled with Cy5.5 to EGFR (1IVO). We synthesized this sequence (black) and attached the Cy5.5 (red) fluorophore via a GGGSK linker (blue) (SEQ ID NO: 18) on the C-terminus, hereafter QRH*-Cy5.5, FIG. 1A. Cy5.5 was chosen for its high quantum yield and photostability. The linker was used to prevent steric hindrance. We developed a scrambled sequence PEHKRRQ (SEQ ID NO: 19) for control, hereafter PEH*-Cy5.5, and found $E_t=-493.1$, FIG. 1B. On the model, QRH*-Cy5.5 binds to amino acids 230-310 of domain 2 of EGFR, FIG. 1C. The EGFR receptor for human and mouse has 97.5% homology in this region. The fluorescence spectra of QRH*-Cy5.5 and PEH*-Cy5.5 at 10 μM concentration in PBS with $X_{ex}=671$ nm excitation revealed a peak emission at 710 nm, FIG. 1D. We purified the Cy5.5-labeled peptides to >97% on HPLC, and measured an experimental mass-to-charge (m/z) ratio on mass spectrometry of 1900.05 for both QRH*-Cy5.5 and PEH*-Cy5.5, FIG. 12A,B, that agreed with expected values.

Synthesis of Peptide Specific for EGFR

We synthesized the Cy5.5-labeled peptides using standard Fmoc-mediated solid-phase synthesis [Fields et al., *Int J Pept Protein Res*, 35:161-214 (1990)]. We used Fmoc and Boc protected L-amino acids, and synthesis was assembled on rink amide MBHA resin. The peptide was synthesized on a PS3 automatic synthesizer (Protein Technologies Inc). The C-terminal lysine was incorporated as Fmoc-Lys (ivDde)-OH, and the N-terminal amino acid was incorporated with Boc protection to avoid unwanted Fmoc removal during deprotection of the ivDde moiety prior to fluorophore labeling. Upon complete assembly of the peptide, the resin was transferred to a reaction vessel for manual labeling with dye. The ivDde side chain protecting group was removed with 5% hydrazine in DMF (3×10 min) with continuous shaking at room temperature (RT). The resin was washed with Dimethylformamide (DMF) and dichloromethane (DCM) 3× each for 1 min. The protected resin-bound peptide was incubated overnight with Cy5.5-NHS ester (Lumiprobe LLC) with DIEA, and the completion of the reaction was monitored by a qualitative Ninhydrin test. Upon completion of labeling, the peptide was cleaved from the resin using TFA:TIS:H2O (95:2.5:2.5 v/v/v; Sigma-Aldrich) for 4 hours with shaking in the dark at RT. After separation of the peptide from the resin, the filtrate was evaporated with $N_2$ gas followed by precipitation with chilled diethyl ether and stored overnight at −20° C. The precipitate was centrifuged at 3000 rpm for 5 min and washed with diethyl ether 3× and centrifuged in between each washing step. The crude peptides were dissolved in 1:1 Acetonitrile/H2O (v/v) and purified by prep-HPLC with a C18 column (Waters Inc) using a water (0.1% TFA)-acetonitrile (0.1% TFA) gradient. The final purity of the peptides was confirmed by analytical C18-column. Further characterization was performed with either ESI (Waters Inc) or Q-TOF (Agilent Technologies) mass spectrometry.

Example 3 siRNA Knockdown of EGFR

We used siRNA to knockdown expression of EGFR in HT29 cells. We used ON-TARGETplus human EGFR siRNA and ON-TARGETplus non-targeting pool (Thermo Scientific) per manufacturer's protocol. 5 μL of siRNA at 5 μM/L concentration was transfected into HT29 cells using DharmaFECT (Thermo Scientific). QRH*-Cy5.5 and PEH*-Cy5.5 were incubated with HT29 siEGFR and siCL cells. The cells were fixed with either 4% PFA or methanol. A 1:1000 dilution of primary monoclonal mouse anti-EGFR antibody (Thermo Scientific, #MS-396, clone 199.12, IgG2a isotype) was incubated overnight at 4° C. Afterwards, the cells were washed 3× with PBS, and further incubated with 1:500 dilution of AF488-labeled secondary goat anti-mouse IgG antibody (Life Technologies, #A-11029) for 1 hour at RT, washed 3×, and then mounted on glass slides with ProLong Gold reagent containing DAPI (Invitrogen). Confocal fluorescence images were collected with FITC, Cy5.5, and DAPI filters using a 63× oil-immersion objective.

Figure 2:
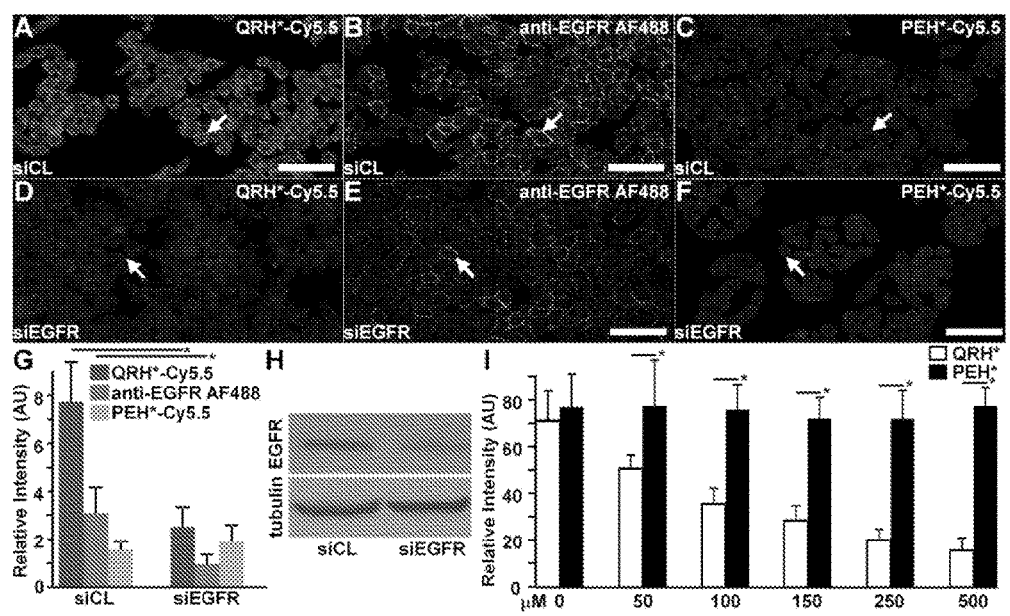
FIG. 2 relates to validation of specific peptide binding to EGFR. Confocal fluorescence images demonstrate strong binding of A) QRH*-Cy5.5 peptide (red) and B) AF488-labeled anti-EGFR (green) to surface (arrow) of control HT29 cells (transfected with non-targeting siRNA, siCL), scale bars 30 μm. C) PEH*-Cy5.5 (red) binding is minimal. D-F) The fluorescence intensities are reduced in knockdown HT29 cells (transfected with siRNA, siEGFR). G) Quantified fluorescence intensities, *P<0.05 by paired t-test. Results are an average of 3 independent measurements. H) Western shows EGFR expression levels. H) On competition, fluorescence intensities (mean±SD) from QRH*-Cy5.5 binding to HT29 cells decrease with addition of unlabeled QRH* in a concentration dependent manner. The addition of unlabeled PEH* show no change, *P<0.05 by paired t-test. Results are an average of 3 independent measurements.

We validated specific binding of QRH*-Cy5.5 to EGFR on siRNA knockdown in HT29 cells. On confocal microscopy, QRH*-Cy5.5 (red), FIG. 2A, and AF488-labeled anti-EGFR (green), FIG. 2B, bind strongly to the surface (arrows) of control HT29 cells (transfected with siCL, non-targeting siRNA), scale bars 30 μm. PEH*-Cy5.5 shows minimal binding, FIG. 2C. Reduced fluorescence intensity was observed for HT29 knockdown cells (transfected with siEGFR, targeting siRNA), FIG. 2D,E. PEH*-Cy5.5 shows minimal binding, FIG. 2F. The results (mean±std) for QRH*-Cy5.5, anti-EGFR AF488, and PEH*-Cy5.5 to control cells (siCL) were 7.8±1.7, 3.1±1.0, and 1.6±0.3 AU, respectively, and to EGFR knockdown cells (siEGFR) were 2.5±0.8, 1.0±0.4, and 1.9±0.7 AU, respectively, *P<0.01 by paired t-test, FIG. 2G. Results are an average of 10 cells from 2 images performed independently. EGFR expression is shown on Western blot, FIG. 12H.

Example 4

Competition for Peptide Binding

Specific binding of QRH*-Cy5.5 to HT29 cells was validated on competitive inhibition with unlabeled QRH* peptide. A total of ~$10^3$ HT29 cells were grown to ~70% confluence on cover slips in triplicate. Unlabeled QRH* and PEH* peptide at 0, 50, 100, 150, 250, and 500 μM were added and incubated with the cells for 30 min at 4° C. The cells were washed and incubated with 5 μM of QRH*-Cy5.5 for another 30 min at 4° C. The cells were washed and fixed with 4% PFA for 5 min. The cells were washed with PBS and mounted with ProLong Gold reagent containing DAPI (Invitrogen). Fluorescence images were collected at each concentration using a 63× objective (Zeiss Axioskop 2 plus microscope), and intensities from 5 cells in 2 independent images were quantified using custom Matlab (Mathworks) software.

Thus, we added unlabeled QRH* to assess binding competition with QRH*-Cy5.5 to HT29 cells. On confocal microscopy, we found the intensities to decrease in a concentration dependent manner, *P<0.01 by paired t-test, FIG. 2I. The addition of unlabeled PEH* (control) showed no change for binding of QRH*-Cy5.5. Results are an average of 3 independent measurements. These results support binding of the peptide rather than the fluorophore to the surface of HT29 cells.

Example 5

Peptide Binding to Colorectal Cancer Cells

We assessed binding of QRH*-Cy5.5 to a panel of colorectal cancer cells that vary in EGFR expression level on confocal microscopy. We observed binding of QRH*-Cy5.5 to the surface (arrows) of HT29, SW480, and SW620 cells with decreasing strength, FIG. 3A-C, scale bars 30 μm. Minimal binding was observed for PEH*-Cy5.5 (control), FIG. 3D-E. The results (mean±std) for QRH*-Cy5.5 binding to HT29, SW480, and SW620 were 3.6±0.6, 2.4±0.4, and 1.0±0.3, respectively, and that for PEH*-Cy5.5 were 1.7±0.4, 1.2±0.3, and 0.8±0.3, respectively, *P<0.01 by paired t-test, FIG. 3G. Results are an average of 10 cells from 2 independent images. EGFR expression is shown on Western blot, FIG. 3H.

Example 6

Characterization of Peptide Binding

We measured the apparent dissociation constant of the peptide to HT29 cells as an assessment of binding affinity.

QRH*-Cy5.5 was serially diluted in PBS at concentrations of 0, 10, 25, 50, 75, 100, 125, 150 and 200 nM. HT29 cells (~$10^5$) were incubated with QRH*-Cy5.5 at 4° C. for 1 hour, washed with cold PBS, and the mean fluorescence intensities were measured on flow cytometry. The equilibrium dissociation constant $k_d=1/k_a$ was calculated by performing a least squares fit of the data to the non-linear equation $I=(I_0+I_{max}k_a[X])/(I_0+k_a[X])$. $I_0$ and $I_{max}$ are the initial and maximum fluorescence intensities, corresponding to no peptide and at saturation, respectively, and [X] represents the concentration of the bound peptide [Thomas et al., *Clin Exp Metastasis*, 26:105-119 (2009)]. Origin 6.1 data analysis software (OriginLab Corp) was used to calculate $k_d$.

We measured the apparent association time constant of the peptide to HT29 cells as an assessment of binding onset. HT29 cells were grown to ~80% confluence in 10 cm dishes, and detached with PBS-based cell dissociation buffer (Invitrogen). Cells (~$10^5$) were incubated with 5 µM QRH*-Cy5.5 at 4° C. for various time intervals ranging from 0 to 20 min. The cells were centrifuged, washed with cold PBS, and fixed with 4% PFA. Flow cytometry analysis was performed as described above, and the median fluorescence intensity (y) was ratioed with that of HT29 cells without addition of peptide at different time points (t) using Flowjo software. The rate constant k was calculated by fitting the data to a first order kinetics model, $y(t)=I_{max}[1-\exp^{(-kt)}]$, where $I_{max}$=maximum value,[60] using Prism 5.0 software (GraphPad Inc).

Figure 3:
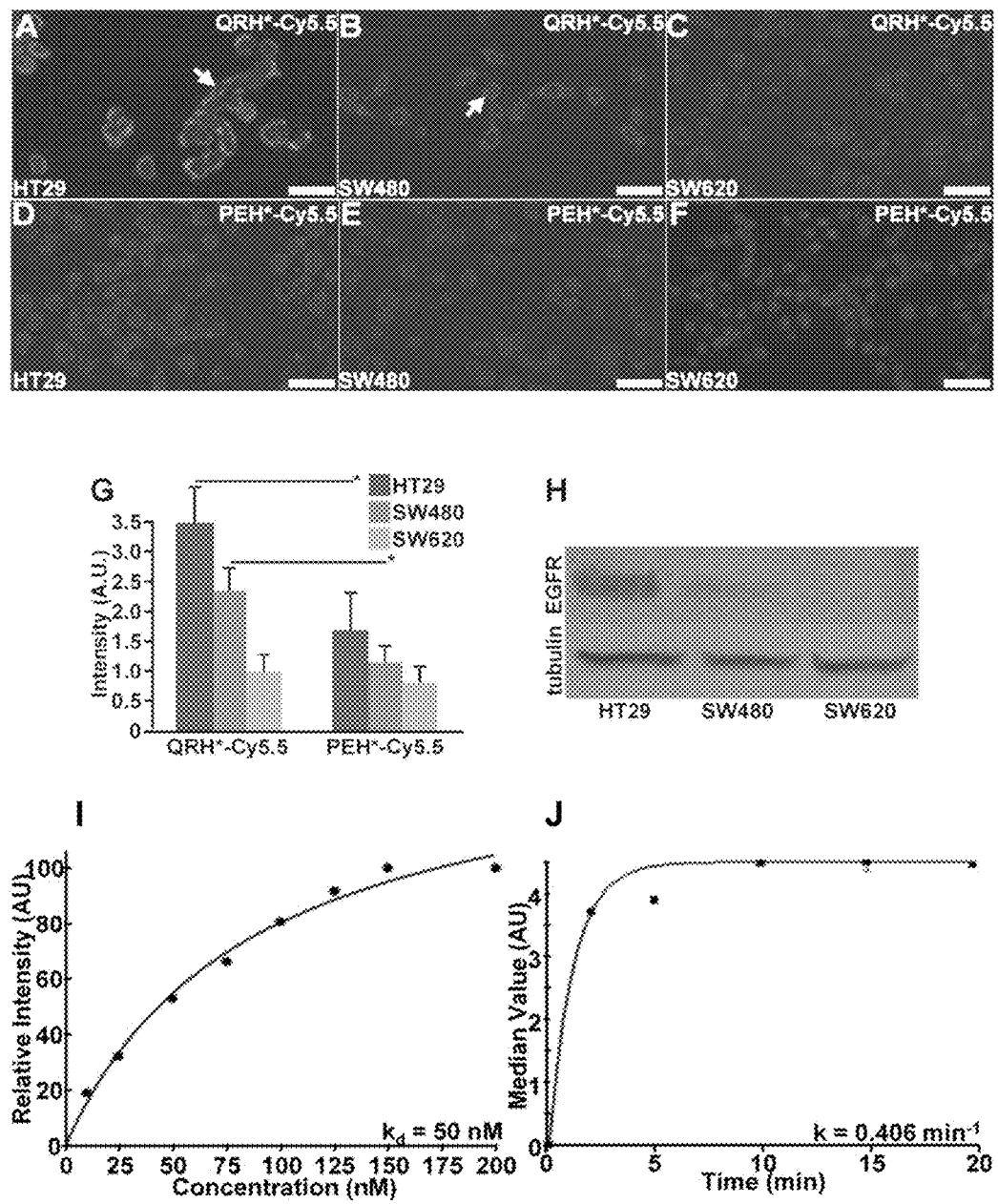
FIG. 3 relates to characterization of EGFR peptide binding parameters. A-F) On confocal microscopy, binding of QRH*-Cy5.5 to cell surface (arrow) of A) HT29, B) SW480, and C) SW620 cells decreases sequentially, scale bars 30 µm. D-F) Minimal signal is observed for PEH*-Cy5.5. G) Quantified fluorescence intensities (mean±SD), *P<0.05, paired t-test. Results are an average of 3 independent measurements. H) Western shows EGFR expression levels. I) Apparent dissociation constant $k_d$=50 nM, $R^2$=0.95 measured for QRH*-Cy5.5 to HT29 cells provides binding affinity. Result is representative of 6 independent experiments. J) Apparent association time constant k=0.406 min-1 (onset of 2.46 min) measured for QRH*-Cy5.5 to HT29 cells provides binding onset. Result is representative of 6 independent experiments.

Thus, we measured an apparent dissociation constant of QRH*-Cy5.5 to HT29 cells of $k_d$=50 nM, $R^2$=0.95 on flow cytometry, FIG. 3I. This result provides a measure for binding affinity, and is representative of 6 independent experiments. Also, we measured an apparent association time constant for QRH*-Cy5.5 to HT29 cells of k=0.406 min$^{-1}$ on flow cytometry, FIG. 3J. This result provides binding time scale of 2.46 min, and is representative of 6 independent experiments.

Example 7

Co-Localization of EGFR Peptide and Antibody Binding

We evaluated co-localization of binding by the QRH*-Cy5.5 peptide and a validated anti-EGFR antibody on cells that overexpress EGFR. A panel of colorectal cancer cells (HT29, SW480, and SW620) was grown on cover slips to ~50% confluence. QRH*-Cy5.5 at 5 µM concentration was incubated with each cell line for 1 hour at 4° C. The cells were washed and fixed with 4% PFA for 5 min. The cells were incubated with primary anti-EGFR antibody and secondary AF488-labeled antibody, as described previously. We applied the peptide rather than the antibody to the cells first because the peptide has a lower affinity and in the lower concentration (<10 µM) is less likely to interfere with antibody binding. Confocal fluorescence images were collected with FITC, Cy5.5, and DAPI filters using a 63× oil-immersion objective.

Figure 13:
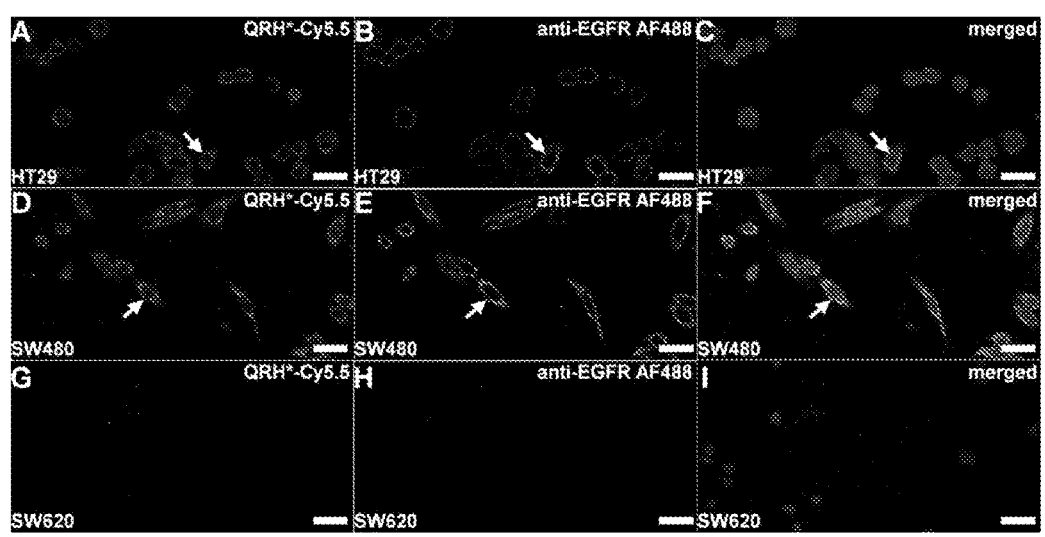
FIG. 13 relates to validation of specific peptide binding to cells. On confocal microscopoy, binding of A) QRH*-Cy5.5 (red) co-localizes with that of B) AF488-labeled anti-EGFR antibody (green) to surface (arrows) of HT29 cells in C) merged image, scale bars 30 µm. D-F) SW480 cells. G-I) SW620 cells. On flow cytometry, binding of QRH*-Cy5.5 to HT29, SW480, and SW620 cells decreases sequentially. Data are representative of 2 independent measurements peptide and antibody to human colonic neoplasia. On confocal microscopy, binding of A) QRH*-Cy5.5 (red) co.

On confocal microscopy, we found binding of QRH*-Cy5.5 (red), FIG. 13A, and AF488-labeled anti-EGFR antibody (green), FIG. 13B, to co-localize on the surface (arrows) of HT29 cells, shown on the merged image, scale bars 30 µm, FIG. 13C. Similar results were found for SW480 cells, FIG. 13D-F. Minimal binding was found for either peptide or antibody on SW620 cells, FIG. 13G-I.

Example 8

Flow Cytometry

HT29, SW480, and SW620 cells were grown to confluence and detached with enzyme-free, PBS-based cell dissociation buffer (Gibco, #13151-014) and cell scrapper. The cells were centrifuged at 1500 rpm for 5 min at 4° C., and then blocked with 0.5% BSA in PBS for 30 min on ice and washed with PBS. ~105 cells were incubated with 5 µM of either QRH*-Cy5.5 or PEH*-Cy5 for 1 hour at 4° C. with mixing. Cells incubated with PBS alone were used as control. The cells were centrifuged again, washed 3× with cold PBS, and fixed on ice with 4% PFA for 10 min. Flow cytometry was performed with ~$10^4$ cells/sample (BD® LSRII, BD Biosciences), and analyzed with the Flowjo software (Tree Star Inc).

We confirmed binding of QRH*-Cy5.5 to HT29, SW480, and SW620 cells in decreasing strength on flow cytometry, FIG. 13J-L. QRH*-Cy5.5 showed stronger binding to each cell than PEH*-Cy5.5. Results are representative of 2 independent measurements.

Example 9

In Vivo Imaging of Colon in CPC; Apc Mouse

Mouse imaging studies were performed with approval of the University of Michigan Committee on the Use and Care of Animals (UCUCA). The mice were housed in pathogen-free conditions and supplied water ad libitum under controlled conditions of humidity (50±10%), light (12/12 hour light/dark cycle) and temperature (25° C.). Anesthesia was induced and maintained via a nose cone with inhaled isoflurane mixed with oxygen at a concentration of 2-4% at a flow rate of ~0.5 L/min. The colon was first rinsed with tap water to remove mucous and debris. White light illumination was used first to identify anatomic landmarks, including polyps, mucosal folds, colonic segment, and distance of endoscope tip from anus, to register images with histology. The Cy5.5-labeled peptides were delivered at a concentration of 100 µM in a volume of 1.5 mL through the 3 Fr instrument channel. After 5 min for incubation, the colon was rinsed 3× with a tap water to remove the unbound peptides. After imaging was completed, the mice were euthanized. The colon was resected, and divided along the longitudinal axis. Flat lesions and polyps were identified on fluorescence, excised perpendicular to the mucosal surface, and processed for histology (H&E). We collected images from mice (n=5) that ranged in age from 7 to 10 months.

Imaging was performed using a small animal endoscope (Karl Storz Veterinary Endoscopy).[39] A xenon light source provides white light illumination via a fluid light cable. A diode-pumped solid state laser (TechnicaLaser Inc) provides excitation at $\lambda_{ex}$=671 nm. The laser beam is expanded to a diameter of 3 mm to fill the aperture of the light cable. The laser power at the tip of the endoscope is <2 mW. The white light images reflect off a dichroic mirror (Semrock Inc, #FF685-Di02-25×36, $\lambda_c$=685 nm), and are focused by an achromatic doublet (Edmund Optics Inc, #32-323). They pass through a neutral density filter (OD 1), and are detected by a color camera (Point Grey Research, #GX-FW-28S5C-C). The fluorescence images pass through the dichroic and a band pass filter (Semrock Inc, #FF01-716/40-25, $\lambda_c$=716 nm, Δλ=40 nm), and are focused on a monochrome camera (Point Grey Research, #GX-FW-28S5M-C). All videos (1932×1452 resolution) are recorded at 15 frames per sec via a firewire connection.

White light and fluorescence videos were exported in avi format with 24 (RGB) and 8 (grayscale) bit digital resolution for the color and fluorescence images, respectively. Streams that showed minimum motion artifact and absence of debris (stool, mucus) were selected for quantification. Individual frames were exported using custom Matlab software. On the fluorescence images, 3 regions of interest (ROI, 25×25 pixels) were picked at random within the dysplastic lesion and within adjacent areas of normal-appearing mucosa. The mean intensities within these ROI's on the fluorescence images were measured. The target to-background (T/B) ratio for each image was determined by ratioing the mean intensities of these two ROIs.

We evaluated specific binding of QRH*-Cy5.5 to colonic dysplasia in vivo in CPC; Apc mice using a small animal endoscope that is sensitive to NIR fluorescence [Liu et al., Gut, 62: 395-403 (2003)]. This mouse was genetically engineered to somatically delete an Apc allele under Cre regulation, and develops flat and polypoid adenomas spontaneously in the distal colon.[44] This model is representative of human disease because Apc mutations are found in >80% of sporadic colorectal cancers [Rowan et al., Proc Natl Acad Sci USA, 97:3352-3357 (2007)]. A white light image of a polyp (arrow) is shown, FIG. 4A. QRH*-Cy5.5 was topically administered in the distal colon, and allowed to incubate for 5 min. The unbound peptides were rinsed away, and the fluorescence image shows increased intensity in a heterogeneous pattern from the polyp, FIG. 4B. Flat lesions (arrowheads) can also be seen on the left that are not apparent on white light. Normal colonic mucosa shows minimal background. Images were collected using PEH*-Cy5.5 (control) from the same region in this mouse 3 days later, and show minimal signal for either lesion, FIG. 4C. A white light image from the colon of a different animal shows no grossly visible polyps, FIG. 4D. Several flat lesions are seen on fluorescence after use of QRH*-Cy5.5, FIG. 4E. Minimal signal was observed with the PEH*-Cy5.5 control, FIG. 4F.

Figure 4:
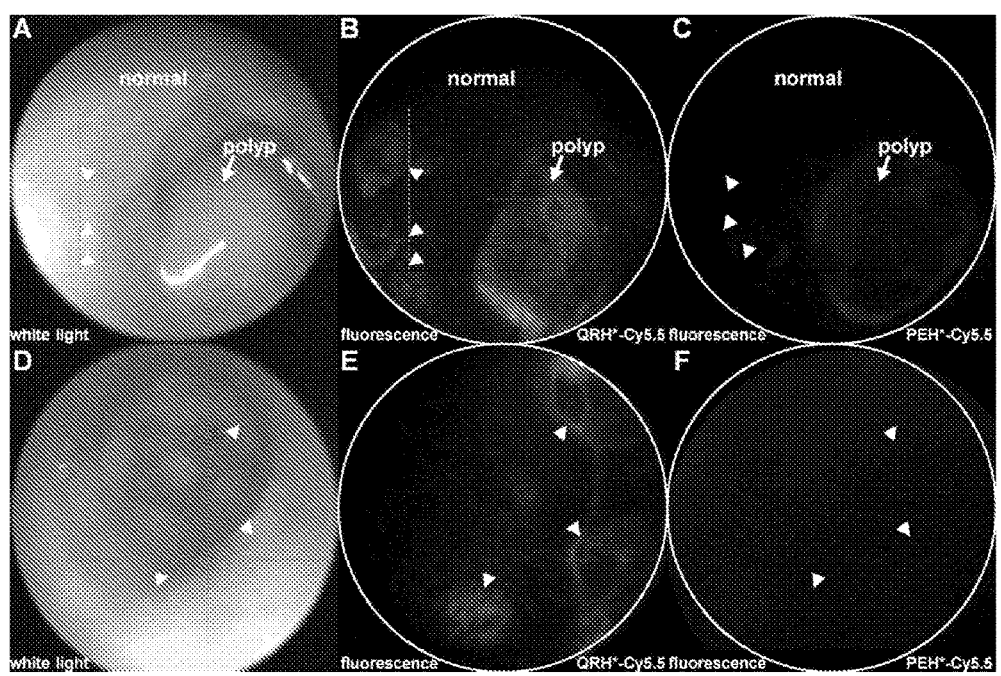
FIG. 4 shows in vivo imaging of colon in CPC; Apc mouse. A) White light image of colon in CPC; Apc mouse shows presence of polyp (arrow). Pathology evaluated along (dashed red) lines. B) NIR fluorescence image after topical administration of QRH*-Cy5.5 shows increased intensity from polyp (arrow) and several flat lesions (arrowheads) with heterogeneous pattern. C) Image with PEH*-Cy5.5 shows minimal signal. D) White light image shows no grossly visible lesions (polyps). E) NIR fluorescence image with QRH*-Cy5.5 shows presence of flat lesions (arrowheads). F) Image with PEH*-Cy5.5 shows minimal signal.
Figure 5:
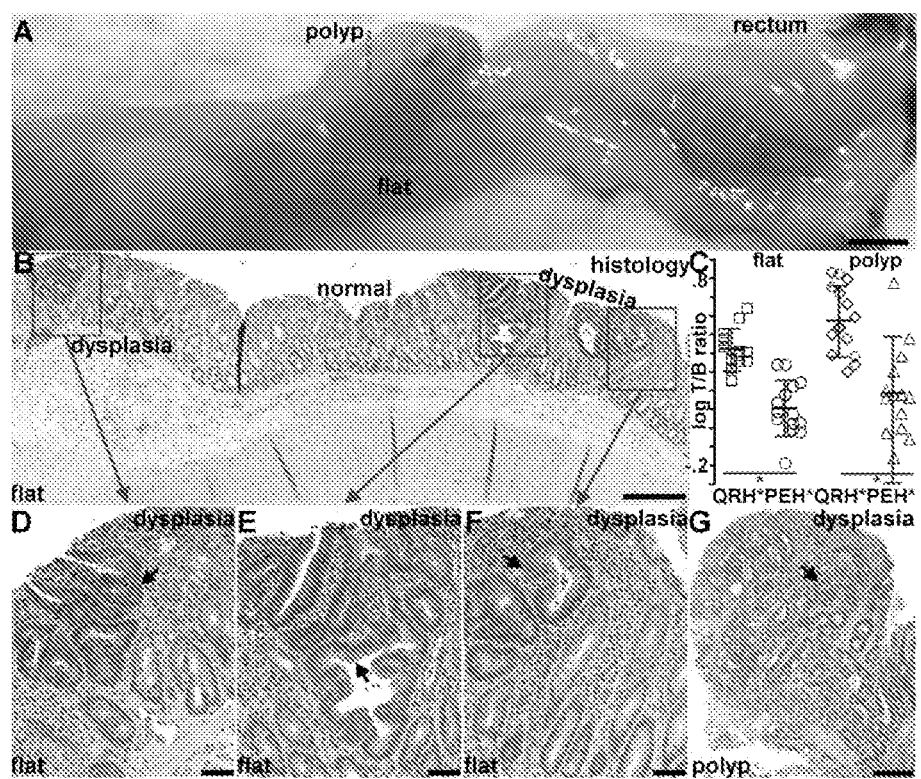
FIG. 5 relates to validation of detection of colonic precancer (dysplasia) on pathology. A) Excised colon from FIG. 4 shows locations of flat lesions and polyp (dashed red lines), scale bar 2 mm. B) Histology (H&E) of flat lesion shows non-polypoid mucosal morphology and foci of dysplasia (red boxes) separated by regions of normal mucosa, scale bar 500 µm. C) T/B ratios (mean±SD) for flat lesions and polyps measured on NIR fluorescence using QRH*-Cy5.5 and PEH*-Cy5.5. D-F) Magnified view of red boxes in B) shows features of dysplasia (arrows), scale bar 100 µm. al Histology (H&E) of polyp along horizontal red line in A) shows dysplasia, scale bar 500 µm.

After completion of imaging, the animals were euthanized and the colon was excised and divided longitudinally. The flat lesions and polyp from FIG. 4 are shown (red lines), scale bar 2 mm, FIG. 5A. Histology (H&E) of the flat lesions cut along the horizontal red line perpendicular to the mucosal surface is shown, scale bar 500 μm, FIG. 5B. The mucosa has a non-polypoid morphology, and foci of flat dysplasia (red boxes) can be seen in between regions of normal mucosa. We measured and log transformed the target-to-background (T/B) ratios on fluorescence for flat dysplasia and polyps in n=5 mice, FIG. 5C. For flat lesions (n=15), the mean (±SD) log of the T/B ratios for QRH*-Cy5.5 and PEH*-Cy5.5 were 0.420±0.103 and 0.108±0.143, *$P=7.4\times10^{-6}$ by paired two-sided t-test. The mean fold-difference was 2.05. For polyps (n=15), the results were 0.572±0.181 and 0.186±0.233, *$P=4.1\times10^{-4}$ by paired two-sided t-test. The mean fold-difference was 2.43. A high magnification view of histology from the flat regions (red boxes) show features of dysplasia (arrows), scale bar 100 μm, FIG. 5D-F. Histology of the polyp also shows features of dysplasia, scale bar 500 μm, FIG. 5G.

EGFR Expression in Flat and Polypoid Dysplasia on Immunohistochemistry

Formalin-fixed sections of mouse colonic mucosa were deparaffinized, and antigen retrieval was performed using standard methods. Briefly, the sections were incubated in xylene for 3 min 3×, washed with 100% ethanol for 2 min 2×, and washed with 95% ethanol for 2 min 2×. Rehydration was performed by washing in dH$_2$O for 5 min 2×. Antigen unmasking was performed by boiling the slides in 10 mM sodium citrate buffer with 0.05% Tween at pH 6.0, and then maintaining at a sub-boiling temp for 15 min. The slides were cooled for 30 min. The sections were washed in dH$_2$O for 3 min 3×, and then incubated in 3% H$_2$O$_2$ in H2O for 10 min. The sections were washed in dH$_2$O for 2 min 3× and in PBST for 5 min. We used two primary anti-EGFR antibodies that cross-react with both mouse and human tissues, including 1:1000 dilution of monoclonal goat anti-mouse (GαM) or 1:500 dilution of polyclonal goat anti-rabbit (GαR) (Cell Signaling Technology, #2232). Blocking was performed with either TBST/5% normal goat serum (GαR) or DAKO protein blocking agent (X0909, DAKO) for 45 min at RT. The sections were incubated overnight at 4° C. and then washed in PBS for 5 min 3×. A 1:200 dilution of secondary antibody (goat anti-mouse or anti-rabbit IgG) was added to each section and incubated for 30 min at RT. The secondary antibody solution was removed by washing with PBS for 5 min 3×. Pre-mixed Elite Vectastain ABC reagent (Vector Labs) was added to each section and incubated for 30 min at RT. The sections were washed in PBST for 5 min 3×, and developed with DAB substrate. The reaction was monitored for 3 min, and then quenched by immersing the slides in dH$_2$O. Hematoxylin was added as a counterstain for ~20 sec, and the sections were dehydrated in increasing concentrations of ethyl alcohol (70%, 80%, 95% 2×, 100% 2×). Coverslips were attached using permount mounting medium (Fisher, #SP15-100) in xylene. Serial sections were processed for histology (H&E). Controls were prepared using secondary antibody, Elite Vectastain ABC reagent, and DAB (without primary anti-EGFR antibody).

Figure 6:
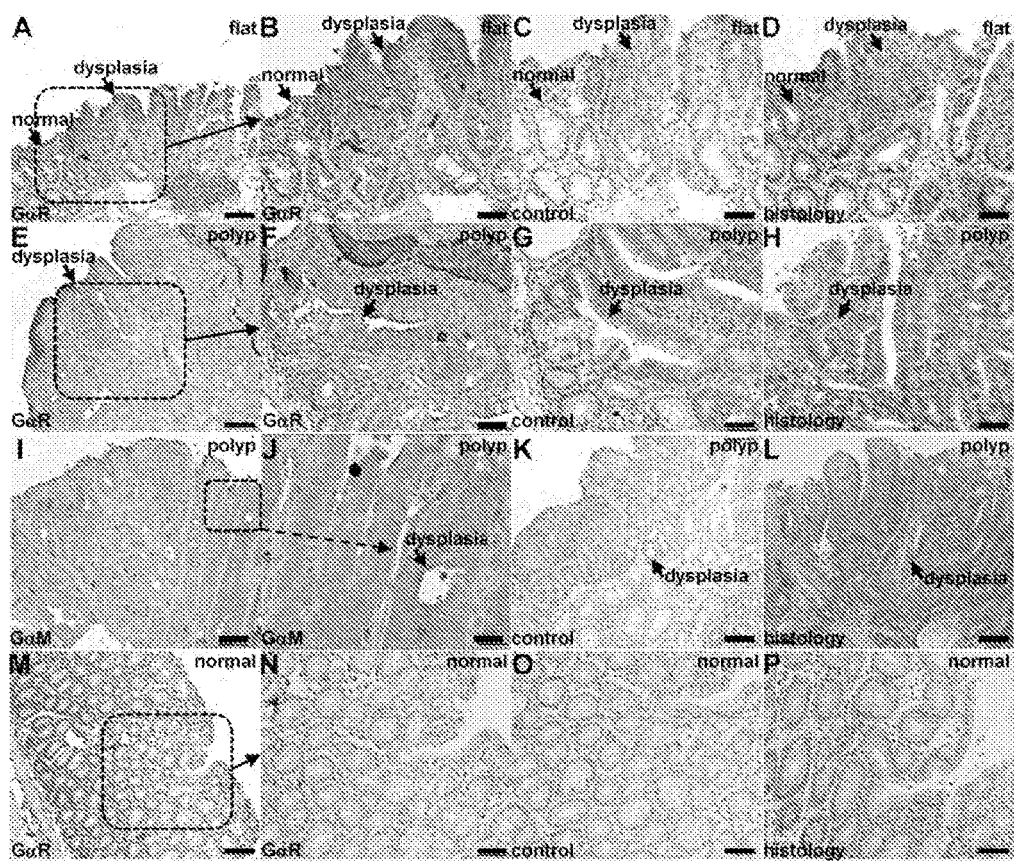
FIG. 6 shows EGFR expression in flat and polypoid dysplasia on immunohistochemistry. A) On immunohistochemistry using primary goat anti-rabbit anti-EGFR antibody (GαR), increased staining was found for dysplasia compared to normal at border of flat colonic lesion, scale bar 200 µm. B) A magnified view of dashed box in A) is shown, scale bar 100 µm. C) Control (no primary antibody). D) Corresponding histology (H&E). E) Strong staining found for dysplastic polyp. F) Magnified view of dashed box in E) is shown. G) Control (no primary antibody). H) Corresponding histology (H&E). I) Strong staining found for dysplastic polyp using primary goat anti-mouse anti-EGFR antibody (GαM), scale bar 200 µm. J) Magnified view of dashed box in I) is shown, scale bar 50 µm. K) Control (no primary antibody), scale bar 100 µm. L) Corresponding histology (H&E). M) Minimal reactivity was found for normal mucosa, scale bar 200 µm. N) Magnified view of dashed box in M) is shown, scale bar 100 µm. O) Control (no primary antibody). P) Corresponding histology (H&E).

We found increased expression of EGFR in dysplasia compared to normal in flat colonic lesions on immunohistochemistry using primary goat anti-rabbit anti-EGFR antibody (GαR), scale bar 200 μm, FIG. 6A. A magnified view of dashed box is shown, scale bar 100 μm, FIG. 6B. An adjacent section was stained with secondary antibody but no primary antibody (control), FIG. 6C. Corresponding histology (H&E) for the flat lesion is shown, FIG. 6D. We also found high expression of EGFR in dysplastic polyps, scale bar 200 μm, FIG. 6E. Magnified view of dashed box is shown, scale bar 100 μm, FIG. 6F. An adjacent section (control) is shown, FIG. 6G. Corresponding histology (H&E) for dysplastic polyp is shown, FIG. 6H. We used primary goat anti-mouse anti-EGFR antibody (GαM) and confirmed increased expression of EGFR in dysplastic polyp, scale bar 200 μm, FIG. 6I. Magnified view of dashed box is shown, scale bar 50 μm, FIG. 6J. An adjacent section (control) is shown, scale bar 100 μm, FIG. 6K. Corresponding histology (H&E) for dysplastic polyp is shown, FIG. 6L. Minimal reactivity was found for normal colonic mucosa on low magnification, scale bar 200 μm, FIG. 6I, and high magnification, scale bar 100 μm, FIG. 6J. An adjacent section (control) is shown, FIG. 6K. Corresponding histology (H&E) for normal is shown, FIG. 6L.

EGFR Expression in Flat and Polypoid Dysplasia on Immunofluorescence.

Specimens of flat dysplasia in mouse colon were formalin fixed and processed as described above. Specimens of polypoid dysplasia in mouse colon were frozen in OCT (Sakura Finetek), cut in 10 μm sections, and incubated with 1:1000 dilution of primary goat anti-mouse anti-EGFR antibody and AF488-labeled secondary antibody, as described previously. The sections were washed 3× with PBS, fixed with 4% PFA for 10 min, washed with PBS 1×, and mounted with Prolong Gold reagent containing DAPI (Invitrogen). Confocal microscopy images were collected with DAPI, AF488, and Cy5.5 filters. Adjacent sections were processed for histology (H&E).

Figure 14:
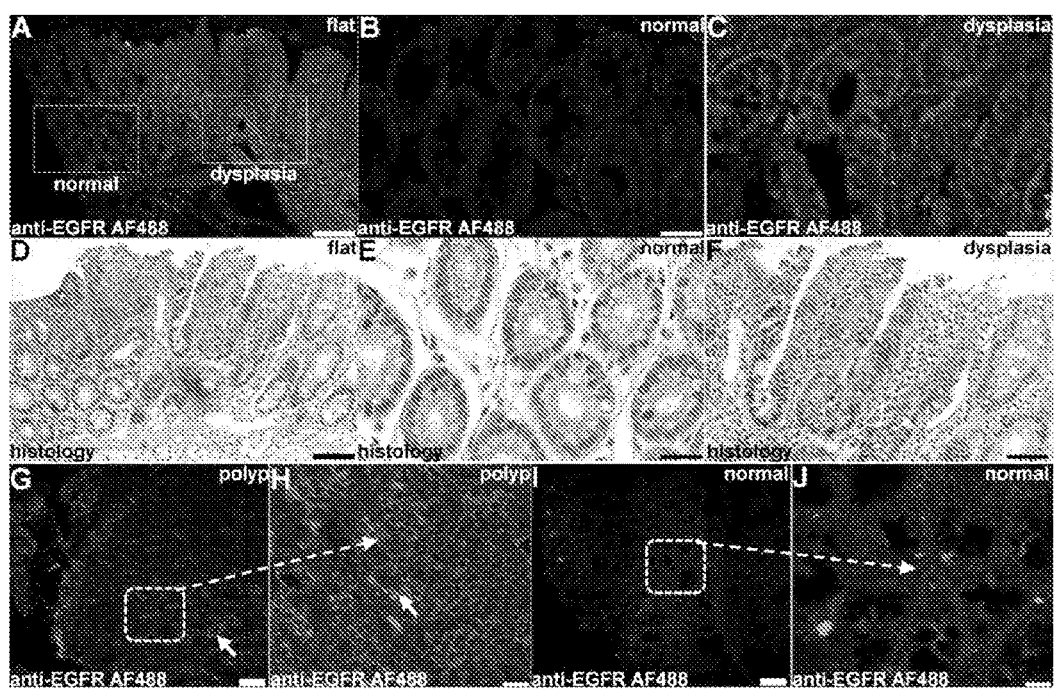
FIG. 14 shows the detection of EGFR expression in flat and polypoid dysplasia on immunofluorescence. On immunofluorescence with AF488-labeled anti-EGFR antibody, A) increased signal was found for dysplasia compared to normal at border of flat colonic lesion, scale bar 100 µm. Magnified view of box in A) for B) normal and C) dysplasia, scale bar 25 µm. D-F) Corresponding histology (H&E), D) scale bar 200, E,F) 100 µm. G) Increased signal was observed for dysplasia from colonic polyp, scale bar 100 µm. H) Magnified view of dashed box in G) show cell surface staining, scale bar 25 µm. I) Minimal EGFR expression was found in normal colonic mucosa, scale bar 100 µm. J) Magnified view of dashed box in I), scale bar 25 µm.

We found increased expression of EGFR in colonic dysplasia on immunofluorescence using formalin-fixed specimens. Contrast between dysplasia and normal can be seen at the border of a flat lesion, scale bar 100 μm, FIG. 14A. A magnified view of the solid boxes in FIG. 14A shows greater fluorescence intensity for dysplasia compared to normal, scale bar 25 μm, FIG. 14B,C. Corresponding histology (H&E) is shown, FIG. 14D-F. We also observed increased fluorescence for binding of QRH*-Cy5.5 to dysplastic crypts (arrow) in polyps using OCT embedded specimens, scale bar 100 μm, FIG. 14G. A magnified view of the dashed box in FIG. 14G shows cell surface staining, scale bar 25 μm, FIG. 14H. Minimal EGFR expression was seen in normal colonic mucosa, scale bar 100 μm, FIG. 14I. A magnified view of dashed box in FIG. 14I is shown, scale bar 25 μm, FIG. 14J.

Example 10

Binding of EGFR Peptide and Antibody to Human Colonic Dysplasia

Specimens of human colonic mucosa were obtained from biopsy during routine colonoscopy, frozen in OCT, cut in 10 μm sections, and incubated with QRH*-Cy5.5 (5 μM) in 1×PBS for 10 min at RT. The sections were washed 3× with PBS and incubated overnight at 4° C. with 1:1000 dilution of primary monoclonal rabbit anti-EGFR antibody (Cell Signaling Technology, #4267, isotype IgG). The sections were washed with PBS 3× and incubated with 1:500 dilution of Alexa Fluor 488-labeled secondary goat anti-rabbit antibody (Invitrogen) for 1 hour at RT. The sections were washed with PBS 3×, and fixed with 4% PFA for 10 min. The sections were then washed with PBS 1×, and mounted with ProLong Gold reagent containing DAPI (Invitrogen). Confocal fluorescence images were collected with DAPI, FITC and Cy5.5 filters with 20× objective (Leica TCS SP5 Microsystems). The mean fluorescence intensities from 3 boxes (dimensions of 30×30 μm2) located completely within the surface epithelium of each specimen were measured. Regions that showed intensity saturation were avoided. Adjacent sections were processed for routine histology (H&E) that was reviewed by two gastrointestinal pathologists (SRO and HDA).

Figure 15:
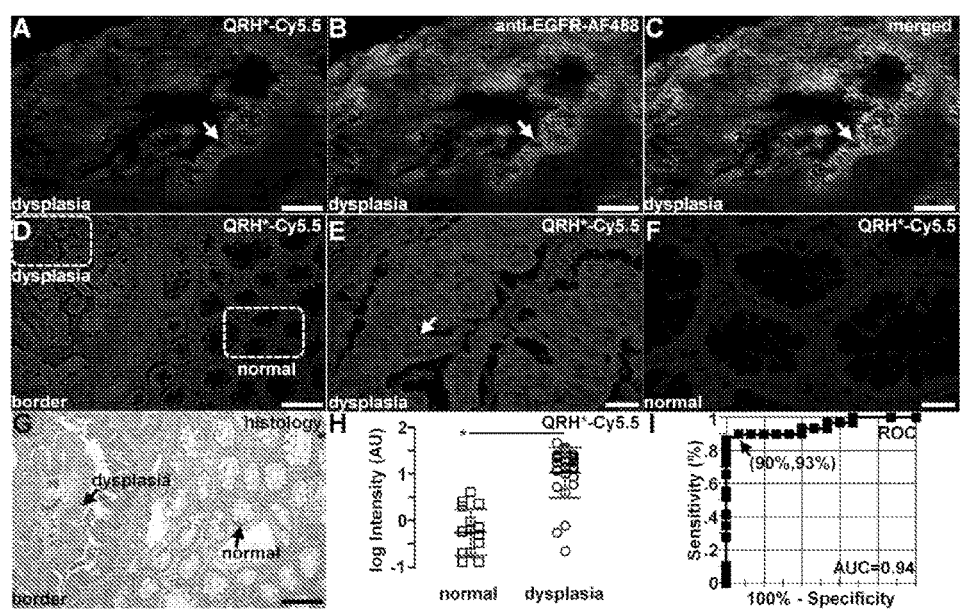
FIG. 15 shows the binding of EGFR peptide and antibody to human colonic neoplasia. On confocal microscopy, binding of A) QRH*-Cy5.5 (red) co-localizes with that of B) AF488-labeled anti-EGFR antibody (green) on surface of dysplastic colonocytes (arrow), shown in C) merged image, p=0.71, scale bars 100 µm. D) Image contrast can be appreciated at lesion border, scale bar 100 µm. Magnified view of boxes in D) is shown for E) dysplasia and F) normal, scale bar 25 µm. G) Corresponding histology (H&E), scale bar 100 µm. H) Log transformed fluorescence intensities show mean (±std) of −0.248±0.49 for normal (n=15) and 1.04±0.54 for dysplasia (n=29) resulting in 19.4 fold difference, *P=3.1×10-9, on unpaired t-test. I) ROC shows sensitivity of 90% and specificity of 93% with an area-under-curve (AUC) of 0.94.

On confocal microscopy of human colonic specimens, we observed binding of QRH*-Cy5.5 (red) and AF488-labeled anti-EGFR (green) to the surface (arrows) of dysplastic colonocytes, scale bars 100 μm, FIG. 15A,B, respectively. Co-localization of peptide and antibody binding can be seen on the merged image, μ=0.71, FIG. 15C. Image contrast between dysplasia and normal can be appreciated at the lesion border, scale bar 100 μm, FIG. 15E. A high magnification view of the white box in FIG. 15D is shown for dysplasia, scale bar 25 μm, FIG. 15E, and normal, FIG. 15F. Corresponding histology (H&E) is shown, scale bar 100 μm, FIG. 15F. The fluorescence intensities were log transformed to improve normality, and the mean (±std) values were found to be −0.248±0.49 for normal (n=15) and 1.04±0.54 for dysplasia (n=29), with *P=$3.1\times10^{-9}$, on unpaired t-test, FIG. 15H. The average fold-change for dysplasia compared to normal was 19.4. The ROC curve shows 90% sensitivity and 93% specificity for distinguishing dysplasia from normal with an area-under-curve (AUC) of 0.94.

Example 11

Binding of EGFR Peptide to Human Esophageal SCC Cells

Figure 7:
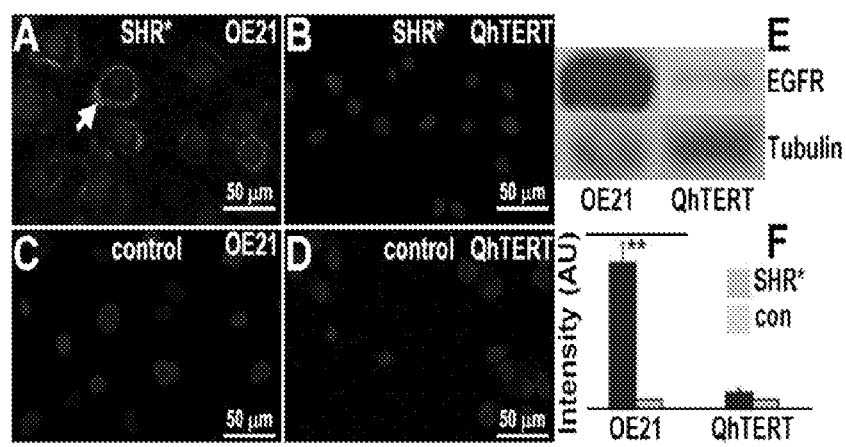
FIG. 7 shows a Western blot illustrating the relative levels of EGFR expression for A) OE21 and B) QhTERT cells. C), D) and E) show controls. F) We quantified the fluorescence intensities on these images in the FITC channel using Matlab (MathWorks, Natick, Mass.) software, and found >5× fluorescence intensity for the SHR* in comparison to the GGG* control peptide for binding to OE21 cells, **P<0.01.

We observed a significantly increased fluorescence intensity for the FITC labeled SHRNRPRNTQPS (SHR*) (SEQ ID NO: 21) peptide on binding to OE21 human esophageal SCC cells in comparison to that for human non-neoplastic QhTERT (control) cells, FIG. 7. Binding of the SHR*-FITC peptide to the membrane (arrow) of OE21 but not to that of QhTERT cells can be seen on confocal fluorescence microscopy (40×), scale bar 50 μm, FIG. 1 (A,B). No binding was seen with the GGG* (control) peptide to either cell, FIG. 7 (C,D).

Figure 8:
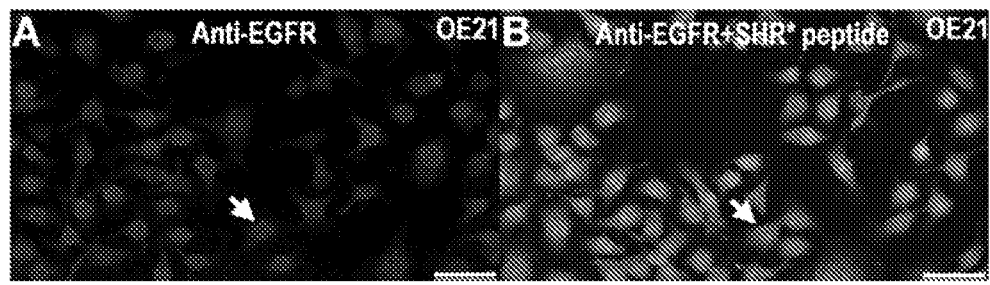
FIG. 8 shows confocal images of A) anti-EGFR antibody (red) staining surface (arrow) of OE21 cells and B) co-localized peptide (green).

We have further validated specific binding of the FITC-labeled peptide to EGFR on co-localization with anti-EGFR antibody. A total of ~$7.5\times10^3$ OE21 cells were grown to ~70% confluence on cover slips and fixed with methanol for 5 min at −20° C. The cells were incubated for 2 hours at RT with 1:500 dilution of primary anti-EGFR mAb (199.12, Neomarkers). The cells were incubated with 1:500 dilution of secondary Cy5.5-labeled antibody for 1 hour at RT, and mounted with ProLong Gold with DAPI (Invitrogen). On confocal microscopy, we observe specific binding of Cy5.5-labeled anti-EGFR antibody (red) to the membrane (arrow) of OE21 cells, FIG. 8A. We then added the FITC-labeled peptide to the OE21 cells. After 10 min for incubation at 37° C., co-localization of the peptide (green) with the antibody (red) to the membrane (arrow) of OE21 cells can be observed, FIG. 8B.

Preferential EGFR peptide binding to human esophageal adenocarcinoma was validated on immunohistochemistry. Over expression of EGFR has been reported in as many as 80% of patients with esophageal adenocarcinoma. Specimens of adenocarcinoma (n=9), intestinal metaplasia (n=6) and squamous esophagus (n=4) were snap frozen, embedded in OCT, cut into 5 μm sections, and placed onto glass slides. The slides were fixed with 4% paraformaldehyde for histology and immunohistochemistry. The slides were blocked with 20% normal mouse serum (Invitrogen, Carlsbad, Calif.) and incubated with the peptide for 1 hour at RT. After rinsing with PBS/0.2% Tween-20 and incubated with HRP-conjugated anti-M13 IgG for another 1 hour, diaminobenzidine (DAB) reagent solution (Sigma, Saint Louis, Mo.) was applied to the sections for 8 min, and the reactions were stopped by washing with PBS. Slides were counterstained with hematoxylin, dehydrated with ethanol, cleared in xylene and sealed with organic mounting media.

Figure 9:
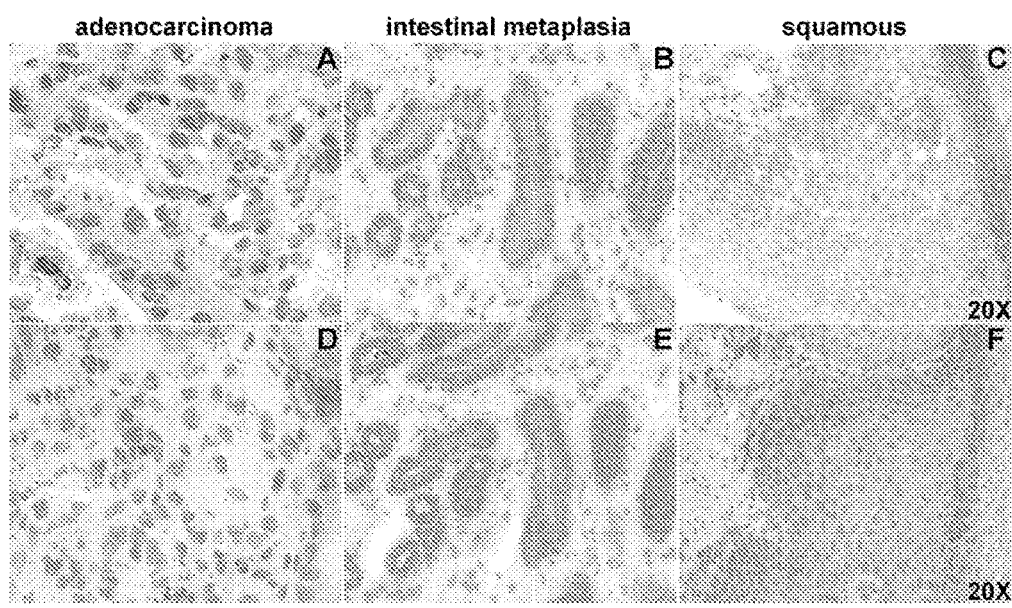
FIG. 9 shows the binding of EGFR peptide to sections of human esophagus adenocarcinoma in comparison to intestinal metaplasia and squamous (normal) tissue.

Positive reactivity was observed on immunohistochemistry in 7/9 sections of human esophageal adenocarcinoma, FIG. 9A, but none was seen in 5/6 sections of intestinal metaplasia, FIG. 9B (one had very weak reactivity) or 4/4 sections of squamous (normal) esophagus, FIG. 9C. The control peptide showed no reaction with adenocarcinoma, intestinal metaplasia or squamous esophagus, FIG. 9D-F.

Figure 16:
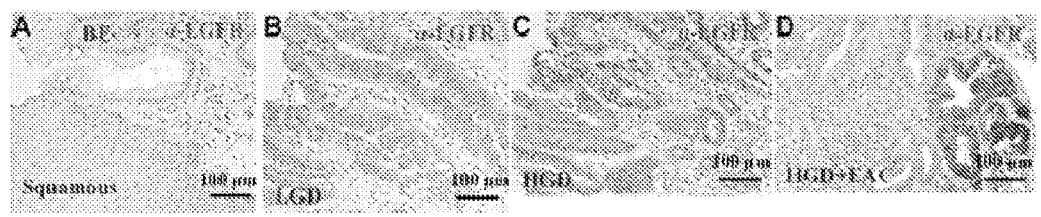
FIG. 16 shows immunohistochemistry performed on human specimens of esophagus using an anti-EGRF antibody. EGFR is overexpressed in neoplasia, including high-grade dyplasia (HGD) and esophageal adenocarcinoma (EAC). This level of expression is much higher than the level in normal squamous (SQ), Barrett's esophagus (BE) and low-grade dysplasia (LGD).
Figure 17:
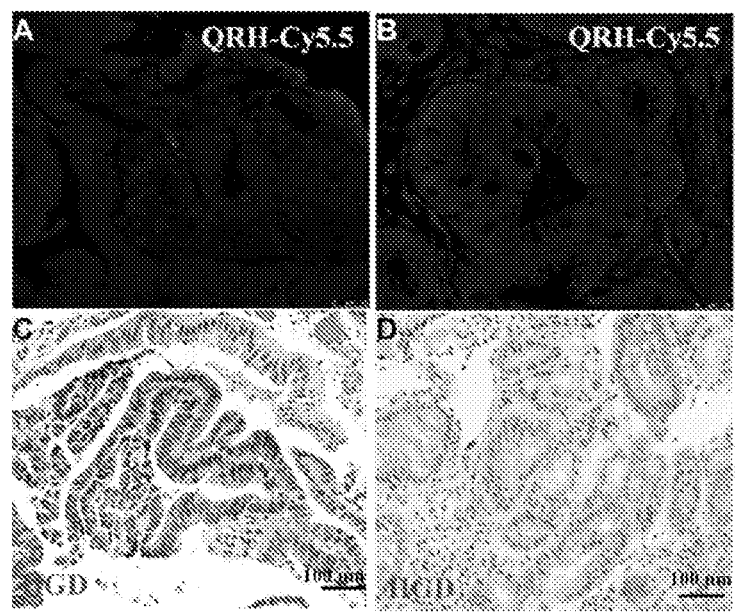
FIG. 17 shows the quantified results for EGFR expression in the different histological classifications of human esophagus on immunohistochemistry.

Over the past three decades, the incidence of esophageal adenocarcinoma (EAC) has risen faster than any other cancer in developed countries. This disease is thought to arise from Barrett's esophagus (BE), a pre-malignant condition whereby normal squamous is replaced by metaplastic columnar epithelium. BE is becoming more common in industrialized societies as a result of a rapid rise in obesity and acid reflux. BE is believed to transform into low-grade dysplasia (LGD) and progress sequentially to high-grade dysplasia (HGD) followed by EAC. We found EGFR to be overexpressed in BE, LGD, HGD and EAC from specimens of human esophagus. See FIGS. 16 and 17.

On endoscopy, dysplasia may be flat in architecture and patchy in distribution. White light endoscopy with random 4-quadrant biopsy is recommended for surveillance, but is prone to sampling errors and false negatives. This protocol has sensitivity ranging from 28% to 85% and specificity ranging from 56% to 100% for detection of HGD and early EAC. Consequently, these guidelines are not wide practiced by community physicians. Surveillance endoscopy is recommended every one to two years. However, the incidence for finding HGD/EAC is quite low, and most patients have many biopsies collected with no evidence of neoplasia on pathology. The diagnosis of dysplasia on pathology is a risk factor for EAC. However, the natural history of this condition is highly variable. The overall risk for progression of LGD to either HGD or EAC is only 13%. Dysplasia may spontaneously regress in some patients, and most patients with BE will not die from EAC.

Use of the peptide reagents described herein is thus contemplated for in vivo imaging to assess esophageal mucosa to guide and prioritize tissue for resection of regions that are most likely to progress on to cancer, to reduce the frequency of surveillance procedures, and to minimize over-diagnosis.

Example 12

Peptide Dimers

Figure 10:
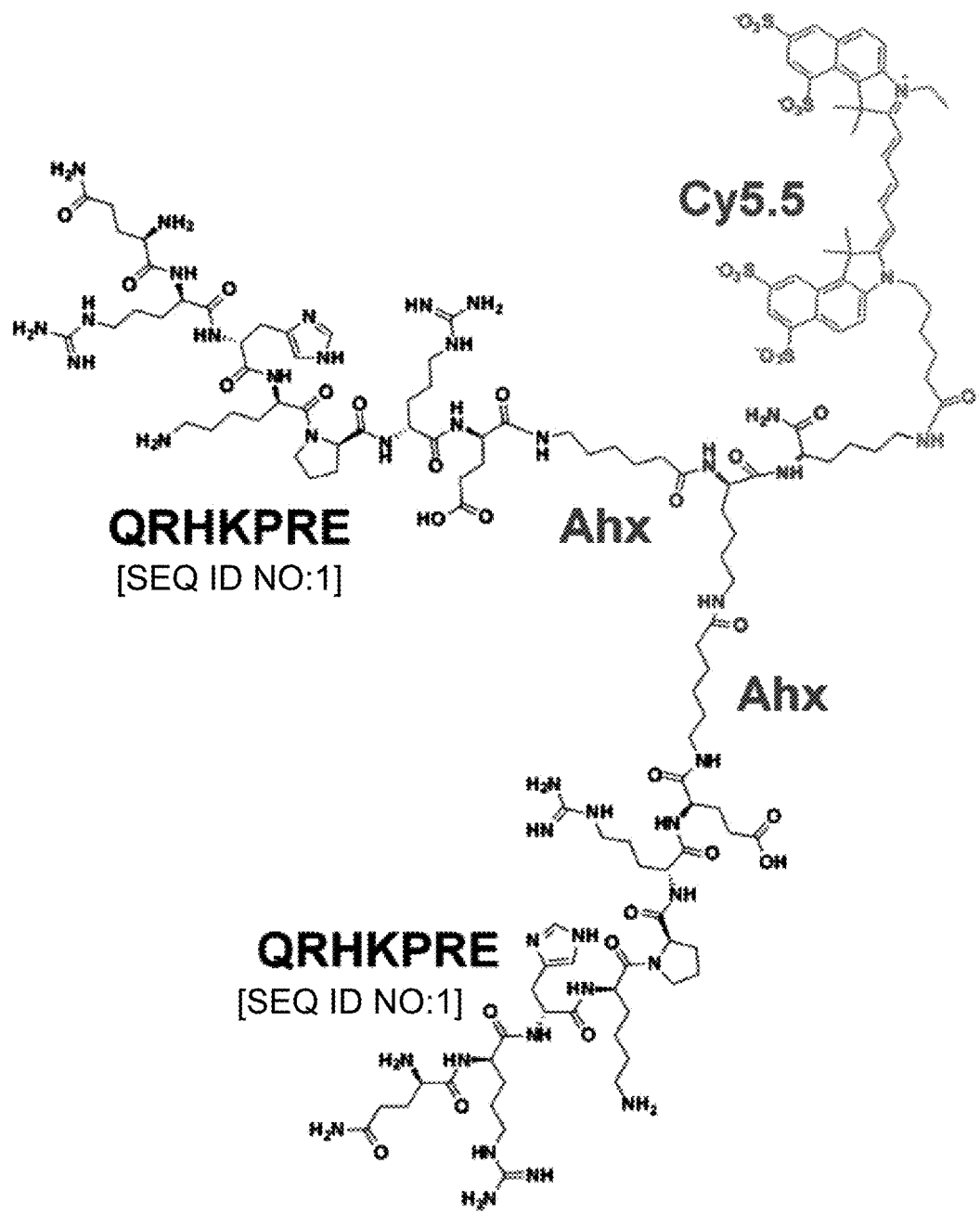
FIG. 10 shows the structure of a peptide QRHKPRE (SEQ ID NO: 1) homodimer labeled with Cy5.5.

Peptide dimers can be synthesized by coupling Fmoc-Lys-(Fmoc) to the resin. An example of the dimer of the QRHKPRE (SEQ ID NO: 1) peptide is shown in FIG. 10 using aminohexanoic acid (Ahx) linkers. Peptide dimers are purified like the monomer peptides using reverse phase-high pressure liquid chromatography. Sequences are confirmed by electrospray ionization (ESI) mass spectroscopy and or matrix-assisted laser desorption/ionization-time of flight mass (MALDI-TOF) spectroscopy. A heterodimer can also be made for targeting two different receptors by coupling with Fmoc-Lys-(Alloc) to the resin.

Example 13

Cholangiocarcinoma (bile duct cancer) is the most common malignancy of the biliary tract, and is increasing in incidence and mortality worldwide. This disease is usually diagnosed at an advanced stage, when the prognosis is poor. Biliary intraepithelial neoplasia (BilIN) represents the precursor condition, and if biliary neoplasms are detected accurately and early, patients can undergo surgical resection with excellent outcomes. Patients suspected of having cholangiocarcinoma frequently present with clinically indeterminate biliary strictures found on transabdominal imaging. However, this finding is non-specific, and could represent either neoplastic or non-neoplastic disease. Because biliary ducts are small in size, the amount of cells and tissues that can be obtained for either cytology or histology is usually insufficient to make a definitive diagnosis. Patients often undergo major surgery or delay therapy only to find either benign strictures, or late stage cancer.

Imaging with peptide reagents described herein is contemplated for use in identifying/detecting BilIN or early-invasive cholangiocarcinoma accurately in indeterminate biliary strictures to guide the physician in making therapeutic decisions. In some embodiments, an imaging approach that can detect multiple targets (multiplexing) is contemplated to achieve high diagnostic performance.

Figure 18:
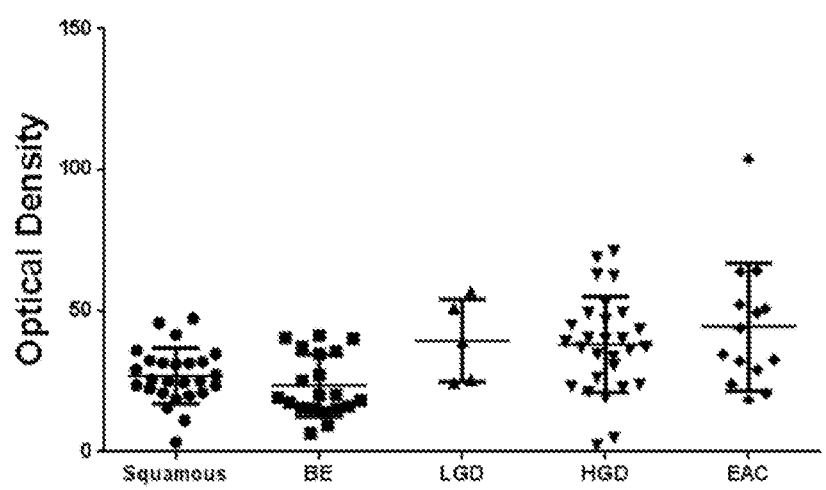
FIG. 18 shows binding of QRH*-Cy5.5 (red) to high-grade dysplasia in human esophagus. A,B) Intense staining of EGFR peptide is seen to high-grade dysplasia (HGD). C,D) Corresponding histology.
Figure 19:
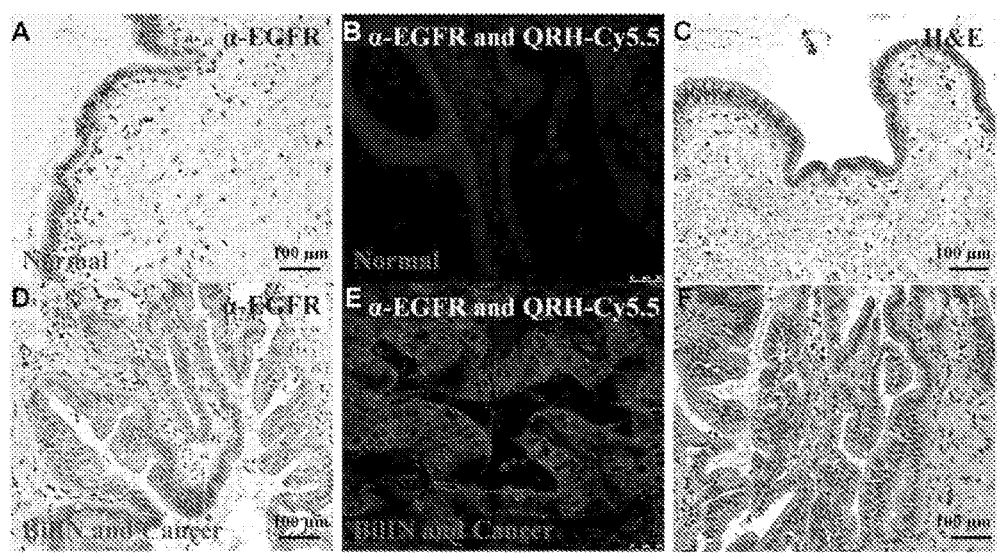
FIG. 19 shows binding of labeled anti-EGFR antibody and/or QRH*-Cy5.5 (red) to human biliary tract epithelium. For normal biliary tract epithelium, A) anti-EGFR antibody shows minimal reactivity on immunohistochemistry; B) minimal staining is seen with FITC-labeled anti-EGFR antibody (green) and QRH*-Cy5.5 (red) on immunofluorescence; and C) corresponding histology is shown. For biliary intraepithelial neoplasia (BilIN) and biliary tract cancer, D) anti-EGFR antibody shows high reactivity to on immunohistochemistry; E) intense staining is seen with fluorescence-labeled anti-EGFR antibody (green) and QRH*-Cy5.5 (red) on immunofluorescence, and F) corresponding histology is shown.

In some embodiments, detection using one or more peptide reagents described herein is contemplated. In some embodiments, use of peptide dimers such as described in Example 12 is contemplated. In some embodiments, detection using a combination of anti-EGFR antibodies and one or more peptide reagents described herein is contemplated. See FIG. 18.

Example 14

Discussion of the Results Described in the Examples

We have identified a novel peptide QRHKPRE (SEQ ID NO: 1) that binds to domain 2 of EGFR. The β-hairpin at this location functions to form dimers rather than to stimulate mitogenic activity, which occurs when EGF docks between domains 1 and 3 [Ogiso et al., *Cell*, 110:775-787 (2002)]. We used a structural model to optimize this sequence to achieve a high affinity, $k_d$=50 nM. Binding occurs rapidly in <2.5 min (k=0.406 min$^{-1}$) with topical administration. This time scale is compatible with future clinical use. We used this peptide to demonstrate in vivo detection of flat colonic lesions that were not seen on white light endoscopy and grossly visible polyps, as well. Furthermore, this peptide was found on immunofluorescence to bind to 90% of specimens of human colonic dysplasia. These results were confirmed on immunohistochemistry using a validated antibody, and support the development of EGFR as an imaging target for early detection of pre-malignant colonic lesions that may currently go undetected on conventional colonoscopy and result in preventable cancers.

Use of topical administration allows the peptides to be delivered in high concentrations to suspect mucosa to maximize binding interactions and achieve optimal image contrast with minimal risk for toxicity. This method results in rapid binding with minimal background, and avoids undesired biodistribution of the probe in other tissues. Peptides specific for EGFR have been developed previously to target therapy of tumors using systemic administration. Because of their small size, peptides are believed to have improved extravasation, increased tissue penetration, and faster clearance in tumors in comparison to antibodies and small molecules. Recombinant CMYIEALDKYAC (SEQ ID NO: 22) was developed based on the structure of the natural EGF ligand and conjugated to doxorubicin [Ai et al., *Moll Pharm*, 8:375-386 (2011)]. Peak accumulation of drug in a tumor xenograft was observed 8 hours after injection. YHWYGYTPQNVI (SEQ ID NO: 23) was selected using phage display technology and found to have a binding affinity of 22 nM. Peak binding activity in a tumor xenograft was observed 4 hours after injection [Li et al., *FASEB J*, 9:1978-1985 (2005)]. LARLLT (SEQ ID NO: 24) was developed using a structural model, synthesized, and conjugated with polyethylene glycol (PEG). This peptide was inserted into a liposome, and was found to have peak accumulation in a tumor xenograft ~80 hours after injection [Song et al., *FASEB J*, 23:1396-1404 (2009)].

For in vivo imaging, we used a mouse model that spontaneously develops colonic adenomas that may have either flat or polypoid architecture. This mouse somatically deletes an Apc allele, and is representative model of human disease because Apc mutations are found in >80% of sporadic colorectal cancers. We performed repetitive imaging using a near-infrared (NIR) fluorescence endoscope to localize the pre-malignant lesions. Cy5.5 was used as the fluorophore because the NIR spectral regime is less sensitive to hemoglobin absorption and tissue scattering, minimizes background from tissue autofluorescence, and provides the maximum light penetration depth. We confirmed expression of EGFR in dysplastic mouse crypts on immunohistochemistry using two validated antibodies. Imaging of EGFR has been performed previously in a mouse orthotopic xenograft model of CRC. Human recombinant EGF was labeled with IRDye 800 CW (NHS ester), and was shown to bind to a mouse xenograft tumor that overexpressesed EGFR on whole body fluorescence imaging. Peak signal was reached 2 days after injection. In vivo imaging has also been performed with a handheld confocal endomicroscope in the cecum of a xenograft mouse model using a FITC-labeled anti-EGFR antibody by exposing the tumor with an abdominal incision [Goetz et al., *Gastroenterology*, 138:435-446 (2010)].

EGFR is overexpressed by many cancers of epithelial origin, including lung [Hirsch et al., *J Clin Oncol*, 21: 3798-3807 (2003)], breast [Bhargava et al., *Mod Pathol*, 18: 1027-1033 (2005)], pancreas [Jimeno et al., *Cancer Res*, 68: 2841-2849 (2008)], head & neck [Reuter et al., *Br J Cancer*, 96: 408-416 (2007)], and esophagus [Hanawa et al., *Int J Cancer*, 118: 1173-1180 (2006)], thus this peptide may also be used for early detection of cancer in other imaging applications. We have previously demonstrated that peptides are safe for clinical use in rigorous animal toxicology studies using Good Laboratory Practices (GLP) and in human studies under an FDA approved Investigational New Drug (IND) application [Sturm et al., *Sci Transl Med*, 5: 184ra61 (2013)]. This new peptide is specific for EGFR, a validated cancer biomarker, and differs from the FITC-labeled peptide VRPMPLQ (SEQ ID NO: 25) that we had previously shown to be specific for dysplastic colorectal polyps on confocal endomicroscopy [Hsiung et al., *Nat Med*, 4: 454-458 (2008)]. The previous peptide was identified using human biopsy specimens as the biopanning substrate rather than a known target, thus its clinical use may not be as widely generalizable. We have selected and validated a peptide that binds specifically to EGFR. This imaging agent is promising for clinical use to target pre-malignant lesions in the colon that are flat in appearance and go undetected on conventional white light colonoscopy that may lead to preventable cancers.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety with particular reference to their disclosure for which they are referred.

We claim:

1. A reagent consisting essentially of a peptide QRHKPRE (SEQ ID NO: 1), HAHRSWS (SEQ ID NO: 2), TYPISFM (SEQ ID NO: 4), KLPGWSG (SEQ ID NO: 5), SHRNRPRNTQPS (SEQ ID NO: 8), NRHKPREKTFTD (SEQ ID NO: 9), TAVPLKRSSVTI (SEQ ID NO: 10), GHTANRQPWPND (SEQ ID NO: 11), LSLTRTRHRNTR (SEQ ID NO: 12), RHRDTQNHRPTN (SEQ ID NO: 13), ARHRPKLPYTHT (SEQ ID NO: 14), KRPRTRNKDERR (SEQ ID NO: 15), or SPMPQLSTLLTR (SEQ ID NO: 16) or a multimer form of the peptide, wherein the peptide specifically binds to epidermal growth factor receptor.

2. The reagent of claim 1 comprising a detectable label attached to the peptide.

3. The reagent of claim 2 wherein the detectable label is detectable by microscopy, photoacoustic, PET, SPECT, ultrasound or magnetic resonance imaging.

4. The reagent of claim 3 wherein the label detectable by microscopy is fluorescein isothiocyanate (FITC).

5. The reagent of claim 3 wherein the label detectable by microscopy is Cy5.

6. The reagent of claim 3 wherein the label detectable by microscopy is Cy5.5.

7. The reagent of claim 3 wherein the label detectable by microscopy is IRdye800.

8. The reagent of claim 1 wherein the multimer form of the peptide is a dimer.

9. The reagent of claim 2 wherein the detectable label is attached to the peptide by a peptide linker.

10. The reagent of claim 9 wherein a terminal amino acid of the linker is lysine.

11. The reagent of claim 10 wherein the linker comprises the sequence GGGSK set out in SEQ ID NO: 18.

12. The reagent of claim 1 comprising a therapeutic moiety attached to the peptide.

13. The reagent of claim 12 wherein the therapeutic moiety is chemotherapeutic agent.

14. A composition comprising the reagent of claim 1, and a pharmaceutically acceptable excipient.

15. A kit for administering the composition of claim 14 to a patient in need thereof, said kit comprising the composition of claim 14, instructions for use of the composition and a device for administering the composition to the patient.

16. A peptide consisting of the amino acid sequence QRHKPRE (SEQ ID NO: 1), HAHRSWS (SEQ ID NO: 2), TYPISFM (SEQ ID NO: 4), SHRNRPRNTQPS (SEQ ID NO: 8), NRHKPREKTFTD (SEQ ID NO: 9), TAVPLKRSSVTI (SEQ ID NO: 10), GHTANRQPWPND (SEQ ID NO: 11), LSLTRTRHRNTR (SEQ ID NO: 12), RHRDTQNHRPTN (SEQ ID NO: 13), ARHRPKLPYTHT (SEQ ID NO: 14) or KRPRTRNKDERR (SEQ ID NO: 15).

17. A method for detecting colon pre-cancer, early cancer or cancer in a patient comprising the steps of administering the reagent of claim 1, 2, 3, 4, 5, 6, 7, 8, 9, 10 or 11 to the colon of the patient and detecting binding of the reagent to pre-cancer, early cancer or cancer colon cells.

18. A method for detecting pre-cancer, early cancer or cancer in a patient comprising the steps of administering the reagent of claim 1, 2, 3, 4, 5, 6, 7, 8, 9, 10 or 11 to the patient and detecting binding of the reagent.

19. A method of determining the effectiveness of a treatment for cancer and/or cancer metastasis, or recurrence of cancer in a patient comprising the step of administering the reagent of claim 1, 2, 3, 4, 5, 6, 7, 8, 9, 10 or 11 to the patient, visualizing a first amount of cells labeled with the reagent, and comparing the first amount to a previously-visualized second amount of cells labeled with the reagent,
wherein a decrease in the first amount cells labeled relative to the previously-visualized second amount of cells labeled is indicative of effective treatment.

20. The method of claim 19 further comprising obtaining a biopsy of the cells labeled by the reagent.

21. A method for delivering a therapeutic moiety to dysplastic cells of a patient comprising the step of administering the reagent of claim 12 to the patient.

22. A method for delivering a therapeutic moiety to early cancer cells or cancer cells of a patient comprising the step of administering the reagent of claim 12 to the patient.

* * * * *